(12) United States Patent
Sauer

(10) Patent No.: US 12,268,415 B2
(45) Date of Patent: *Apr. 8, 2025

(54) SURGICAL PORT FOR STAY SUTURES AND SYSTEM AND METHOD THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/209,308

(22) Filed: Jun. 13, 2023

(65) Prior Publication Data

US 2023/0404616 A1 Dec. 21, 2023

Related U.S. Application Data

(63) Continuation of application No. 17/399,670, filed on Aug. 11, 2021, now Pat. No. 11,712,265, which is a continuation of application No. 15/982,669, filed on May 17, 2018, now Pat. No. 11,116,541.

(60) Provisional application No. 62/507,737, filed on May 17, 2017.

(51) Int. Cl.
*A61B 17/34* (2006.01)
*A61B 17/04* (2006.01)
*A61B 17/06* (2006.01)
*A61B 17/00* (2006.01)

(52) U.S. Cl.
CPC ...... *A61B 17/3423* (2013.01); *A61B 17/0482* (2013.01); *A61B 17/0485* (2013.01); *A61B 17/06061* (2013.01); *A61B 17/3421* (2013.01); *A61B 2017/00477* (2013.01); *A61B 17/0469* (2013.01); *A61B 2017/3445* (2013.01)

(58) Field of Classification Search
CPC ........ A61B 17/3423; A61B 2017/0451; A61B 2017/06142; A61B 17/0482; A61B 17/0485; A61B 17/06061; A61B 17/0493
See application file for complete search history.

(56) References Cited

U.S. PATENT DOCUMENTS

| | | | | |
|---|---|---|---|---|
| 5,810,721 A | * | 9/1998 | Mueller | A61B 17/0293 600/206 |
| 5,928,252 A | * | 7/1999 | Steadman | A61B 17/064 606/228 |
| 6,048,309 A | * | 4/2000 | Flom | A61B 17/0293 600/206 |
| 6,066,160 A | * | 5/2000 | Colvin | A61B 17/0487 606/232 |
| 6,190,311 B1 | * | 2/2001 | Glines | A61B 17/0293 600/215 |
| 8,328,717 B2 | * | 12/2012 | Battles | A61B 17/3462 600/206 |
| 11,712,265 B2 | * | 8/2023 | Sauer | A61B 17/06061 600/204 |

(Continued)

*Primary Examiner* — Julianna N Harvey
(74) *Attorney, Agent, or Firm* — Michael E. Coyne

(57) ABSTRACT

A surgical port is disclosed. The surgical port has a cannular channel. The surgical port also has one or more suture slots in communication with the cannular channel. The surgical port further has a pair of cam grips for each of the one or more suture slots, each pair of cam grips comprising opposing gripping arms configured to allow suture to be pulled through the opposing gripping arms in a direction away from the cannular channel and to resist suture movement in a direction towards the cannular channel.

24 Claims, 30 Drawing Sheets

(56) References Cited

U.S. PATENT DOCUMENTS

| | | | |
|---|---|---|---|
| 2001/0025136 A1* | 9/2001 | Leonard | A61B 90/00 |
| | | | 600/210 |
| 2003/0149443 A1* | 8/2003 | Gaskill, III | A61B 17/3421 |
| | | | 606/190 |
| 2005/0222582 A1* | 10/2005 | Wenchell | A61B 17/3462 |
| | | | 606/108 |
| 2009/0044814 A1* | 2/2009 | Iancea | A61B 17/06109 |
| | | | 623/23.72 |
| 2010/0234688 A1* | 9/2010 | Carter | A61B 17/06061 |
| | | | 600/208 |
| 2012/0179001 A1* | 7/2012 | Taylor | A61B 17/3498 |
| | | | 600/208 |
| 2013/0103057 A1* | 4/2013 | Keating | A61B 17/0491 |
| | | | 606/144 |
| 2014/0275798 A1* | 9/2014 | Keating | A61B 17/00234 |
| | | | 600/208 |

* cited by examiner

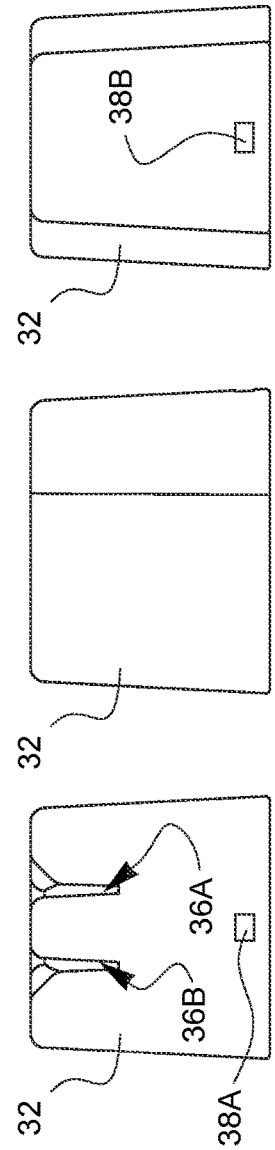
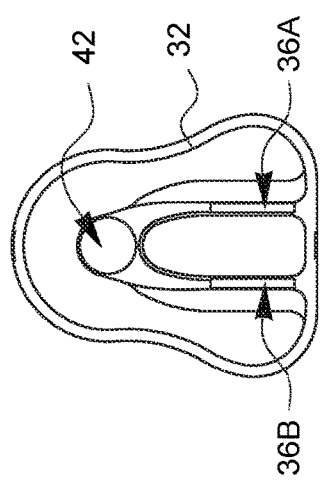
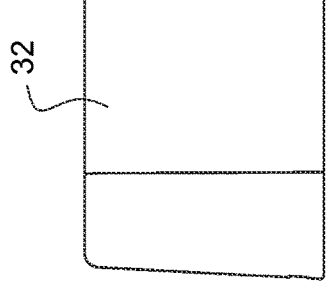
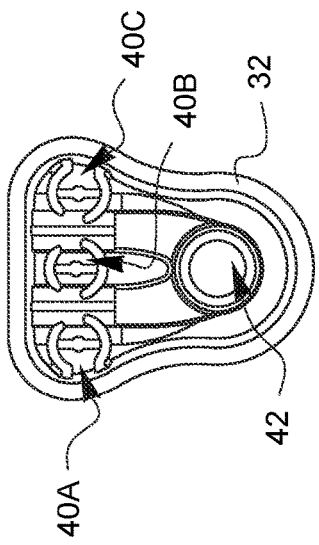
FIG. 2A  FIG. 2B  FIG. 2C  FIG. 2D  FIG. 2E  FIG. 2F

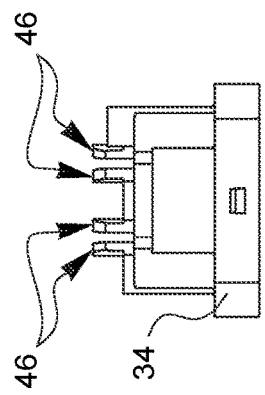
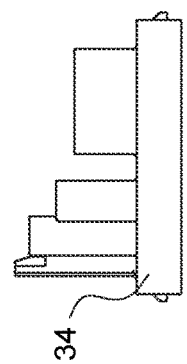
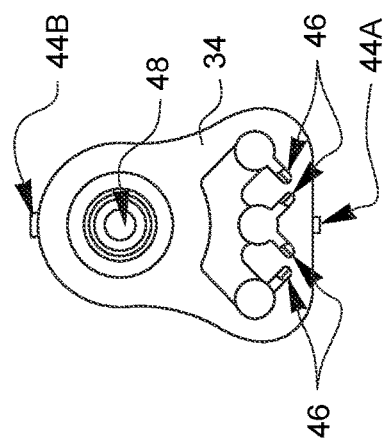
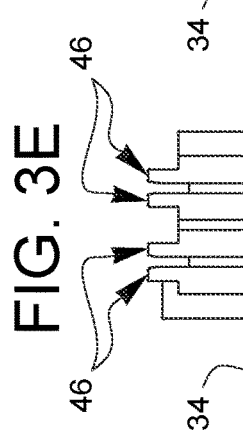
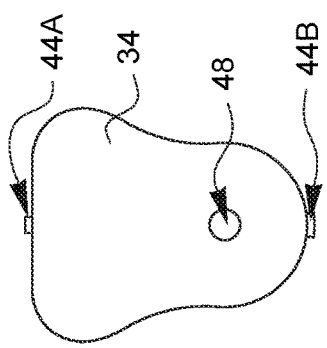
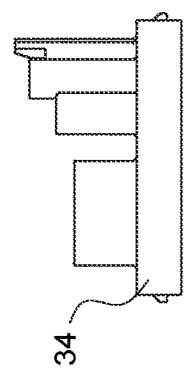

SURGICAL PORT FOR STAY SUTURES AND SYSTEM AND METHOD THEREOF

CROSS-REFERENCE TO RELATED APPLICATIONS

This patent application is a continuation of U.S. patent application Ser. No. 17/399,670, filed on filed Aug. 11, 2021, which is a continuation of U.S. patent application Ser. No. 15/982,669, filed on filed May 17, 2018, which claims priority to U.S. Provisional Patent Application No. 62/507,737, filed May 17, 2017, each of which is incorporated by reference herein in its entirety.

FIELD

The claimed invention relates to surgical devices, and more specifically to surgical ports.

BACKGROUND

Laparoscopic, endoscopic, and other types of minimally invasive surgical procedures often rely on percutaneous introduction of surgical instruments into an internal region of a patient where the surgical procedure is to be performed. As part of many minimally invasive surgical procedures, stay sutures may be placed in various tissue and then tensioned either to pull the tissue out of the way or to move the tissue to a more convenient position for the surgeon to reach through a minimally invasive incision. Surgeons continue to find it desirable to utilize smaller and smaller access incisions in order to minimize trauma and reduce patient recovery times. Unfortunately, in some situations, the minimally invasive access incision is so narrow that it does not provide a suitable angle for stay sutures to pull tissue away from the access channel afforded by the minimally invasive incision. Therefore, it would be desirable to have an improved device for routing the stay sutures separately from a main surgical access point while enabling convenient adjustment of the stay suture tensions.

SUMMARY

A surgical port is disclosed. The surgical port has a cannular channel. The surgical port also has one or more suture slots in communication with the cannular channel. The surgical port further has a pair of cam grips for each of the one or more suture slots, each pair of cam grips comprising opposing gripping arms configured to allow suture to be pulled through the opposing gripping arms in a direction away from the cannular channel and to resist suture movement in a direction towards the cannular channel.

BRIEF DESCRIPTION OF THE DRAWINGS

FIGS. 2A, 2B, 2C, 2D, 2E, and 2F are front, left side, right side, rear, top, and bottom elevational views, respectively, of an upper flange cover for the surgical port of FIG. 1.

FIGS. 3A, 3B, 3C, 3D, 3E, and 3F are front, left side, right side, rear, top, and bottom elevational views, respectively, of a lower flange of the surgical port of FIG. 1.

Figure 1:
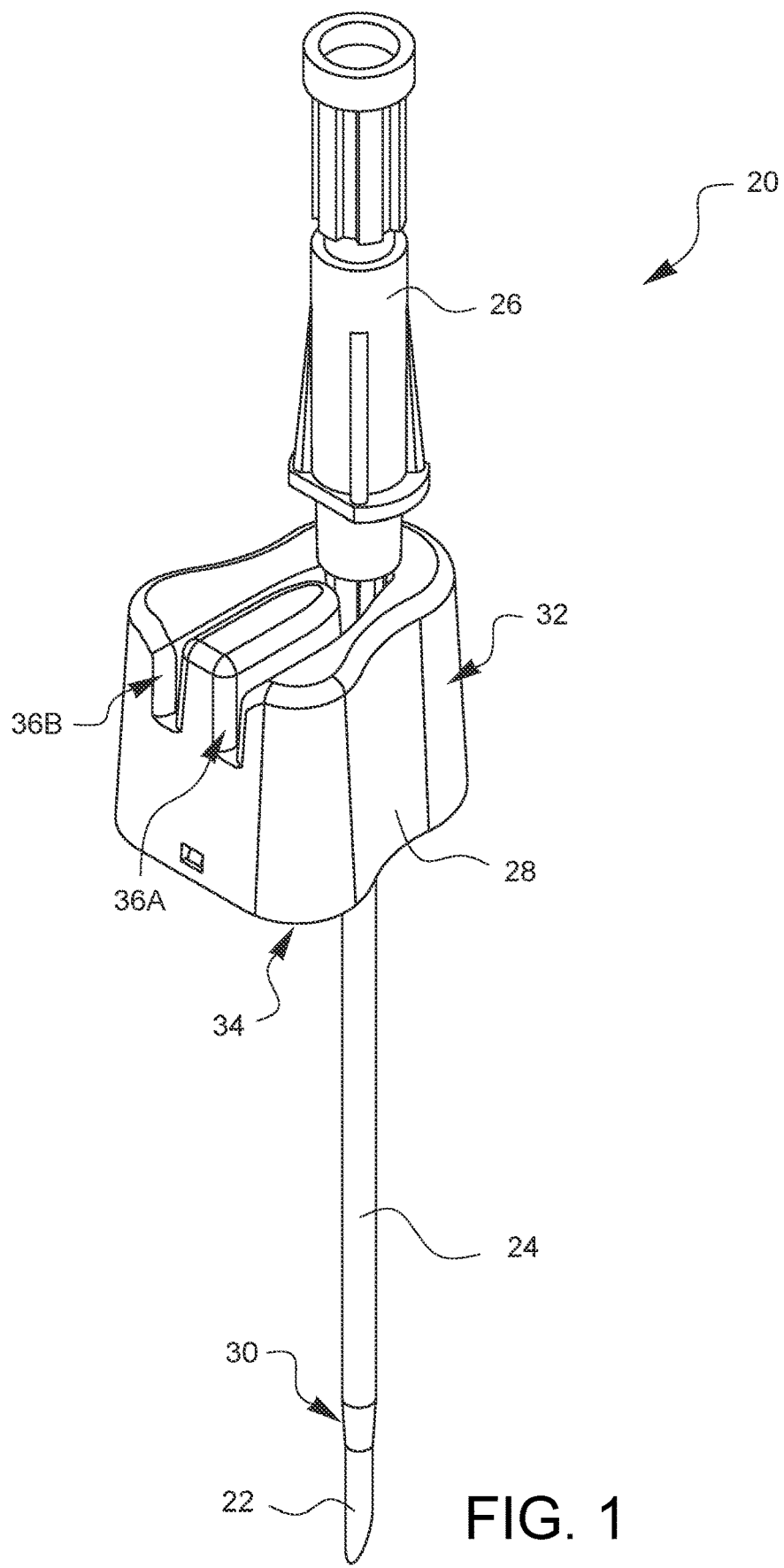
FIG. 1 illustrates one embodiment of a surgical port having one embodiment of a needle installed therein.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 illustrates one embodiment of a surgical port 20 having one embodiment of a needle 22 installed therein. The tip of the needle 22 can be seen extending from a cannular channel 24 of the surgical port 20. The needle 22 has a handle 26 which is sized to prevent the handle 26 from passing through the cannular channel 24. The cannular channel 24 is coupled to a flange 28.

In practice, the needle 22 is installed in the surgical port 20 when it is desired to place the surgical port 20 into a patient. Alternatively, the needle 22 may come pre-installed in the surgical port 20 as shown in FIG. 1. The cannular channel 24 may be flexible, and if so, the inserted needle 22 provides some stiffness to the cannular channel 24. As configured in FIG. 1, the needle may be used to pierce through the skin, which tends to be tougher to pass through than the tissues beneath the skin. When the skin is just pierced and the distal end 30 of the cannular channel 24 has passed through the skin, the needle 22 may be removed from the surgical port 20 by pulling on the needle handle 26 and holding the flange 28 steady. If the cannular channel 24 is stiff enough, the flange 28 may be used to push the distal end 30 of the cannular channel 24 through internal tissue, for example, muscle tissue until the flange 28 rests on the outer surface of the patient. Alternately, and especially if the cannular channel 24 is not rigid, a blunt obturator (not shown in FIG. 1) may be inserted into the cannular channel 24 in place of the needle 22. The distal tip of such a blunt obturator could extend past the distal end of the cannular channel 24 and could be used to insert the cannular channel 24 of the surgical port through the tissue below the skin. The blunt obturator would tend to avoid harming the tissue through which it passed.

Once the cannular channel 24 reaches a desired position, the obturator (if used) could be removed. The access opening created by the cannular channel 24 can be on the order of 1-2 mm or smaller, creating very little trauma to the patient.

With the surgical port 20 in place, a snare or hook sized to fit within the cannular channel 24 may be inserted into the patient through the cannular channel 24 in order to capture stay suture ends which have been stitched through tissue. The stay suture stitches would typically have been placed via access from the main minimally invasive incision. It is desirable, however, to be able to pull the stay sutures at an angle different from that provided by the minimally invasive incision. Therefore, if the stay suture ends are captured by a hook or snare placed through the cannular channel 24 of the surgical port 20, the stay suture ends may be pulled through the cannular channel 24 and out of the surgical port 20.

In this embodiment, the flange 28 is made from an upper flange cover 32 and a lower flange 34 (which is not visible in the view of FIG. 1). The flange 28 defines multiple suture slots 36A, 36B.

FIGS. 2A, 2B, 2C, 2D, 2E, and 2F are front, left side, right side, rear, top, and bottom elevational views, respectively, of the upper flange cover 32. The upper flange cover 32 defines tab receiving openings 38A and 38B which are visible in the front and rear views, respectively, of FIGS. 2A and 2D. The tab receiving openings 38A, 38B are configured to attach to corresponding tabs on the lower flange 34 (not visible in FIGS. 2A-2F). In this embodiment, the upper flange cover 32 also defines three cam pockets 40A, 40B, 40C, the features of which will be discussed in more detail later in this specification. The upper flange cover 32 also defines an opening 42 which works in conjunction with a similar opening in the lower flange to couple and communicate with the cannular channel.

FIGS. 3A, 3B, 3C, 3D, 3E, and 3F are front, left side, right side, rear, top, and bottom elevational views, respectively, of the lower flange 34. The lower flange has tabs 44A, 44B which are configured to correspond and couple to tab receiving openings 38A, 38B for coupling the lower flange 34 to the upper flange cover. The lower flange 34 also has a plurality of cam stops 46, the features of which will be discussed in more detail later in the specification. The lower flange 34 also defines an opening 48 which is configured to receive a portion of the cannular channel.

Figure 4A:
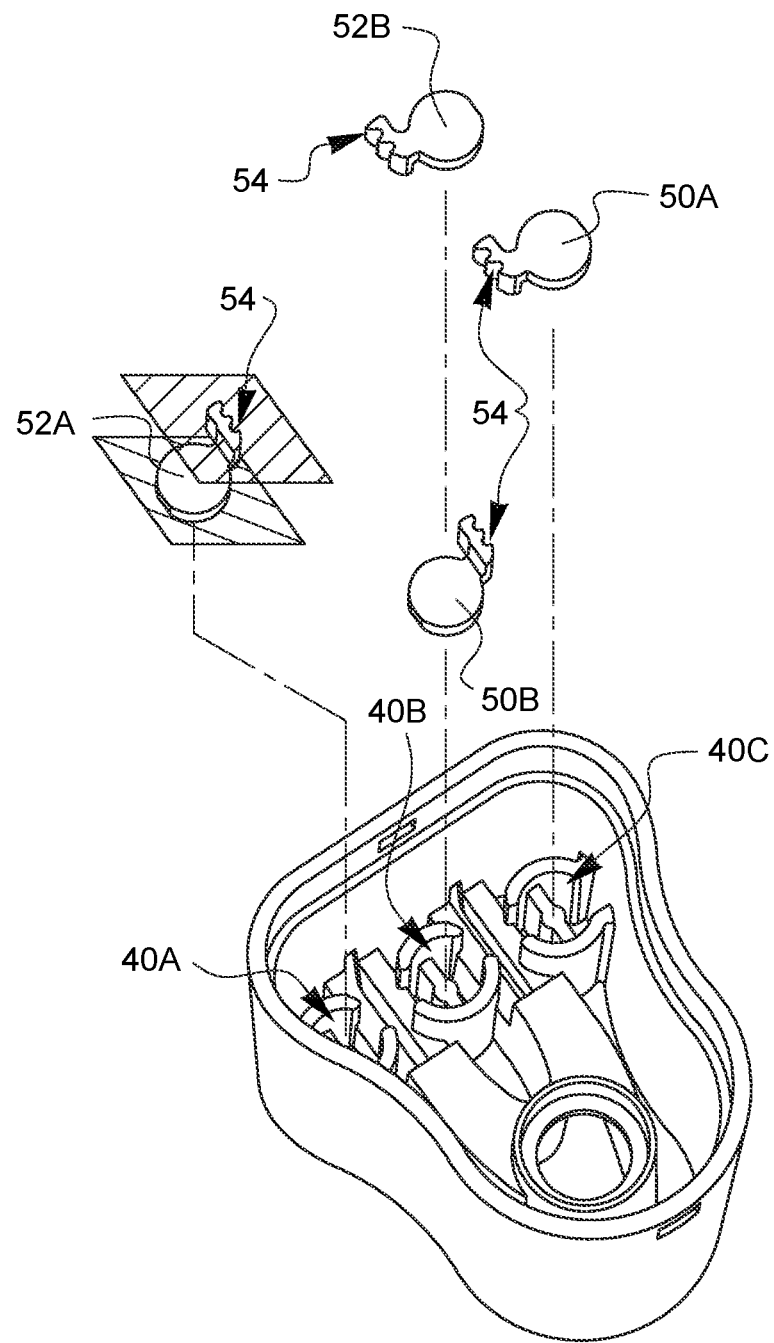
FIGS. 4A-4D are exploded views illustrating the assembly of one embodiment of a surgical port.

FIGS. 4A-4D are exploded views illustrating the assembly of one embodiment of a surgical port. As shown in FIG. 4A, one or more cam grips 50A, 50B, 52A, 52B are set into the cam pockets 40A, 40B, 40C of the upper flange cover 32. Specifically in this embodiment, cam grip 50A is set into cam pocket 40C; cam grip 50B and then cam grip 52B are set into cam pocket 40B; and cam grip 52A is set into cam pocket 40A. Each cam grip has a gripping arm 54. The gripping arms 54 of cam grips 50A and 50B face each other, while the gripping arms 54 of cam grips 52A and 52B face each other. The pair of gripping arms 54 on cam grips 50A and are aligned to lie in substantially the same plane. Similarly, the pair of gripping arms 54 on cam grips 52A and 52B are aligned to lie in substantially the same plane. In this particular embodiment, all of the gripping arms 54 will lie in substantially the same plane. Since cam grips 50B and 52B are both installed in the same cam pocket 40B, all of the gripping arms 54 are made to lie in the same plane by making cam pockets 40A, 40B deeper than cam pocket 40C, and also by extending the gripping arms 54 of cam grips 52A and 50B higher than the gripping arms 54 of cam grips 50A and 52B. In other embodiments, the pairs of gripping arms may lie in different planes.

Figure 4B:
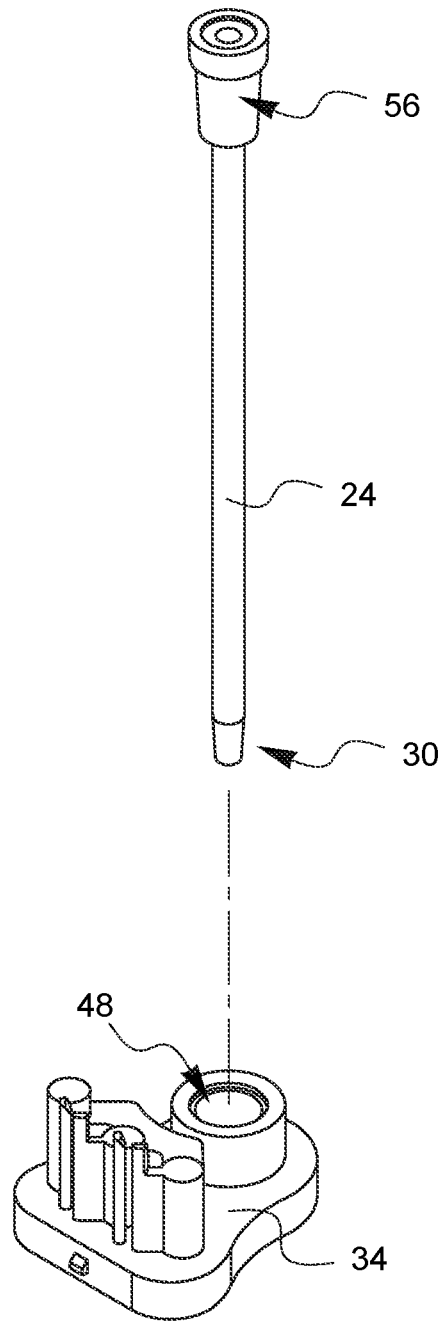

As shown in FIG. 4B, the distal end 30 of the cannular channel 24 is inserted into the upper side of the opening 48 in the lower flange 34. In this embodiment, the cannular channel 24 has a stepped proximal end 56 which corresponds to the shape of opening 48 and is configured to prevent the proximal end 56 from passing all the way through opening 48 in the lower flange 34. These components may be held together until further assembly, or they may be coupled together using a variety of techniques, including, but not limited to gluing, ultrasonic welding, press fitting, and heat bonding.

Figure 4C:
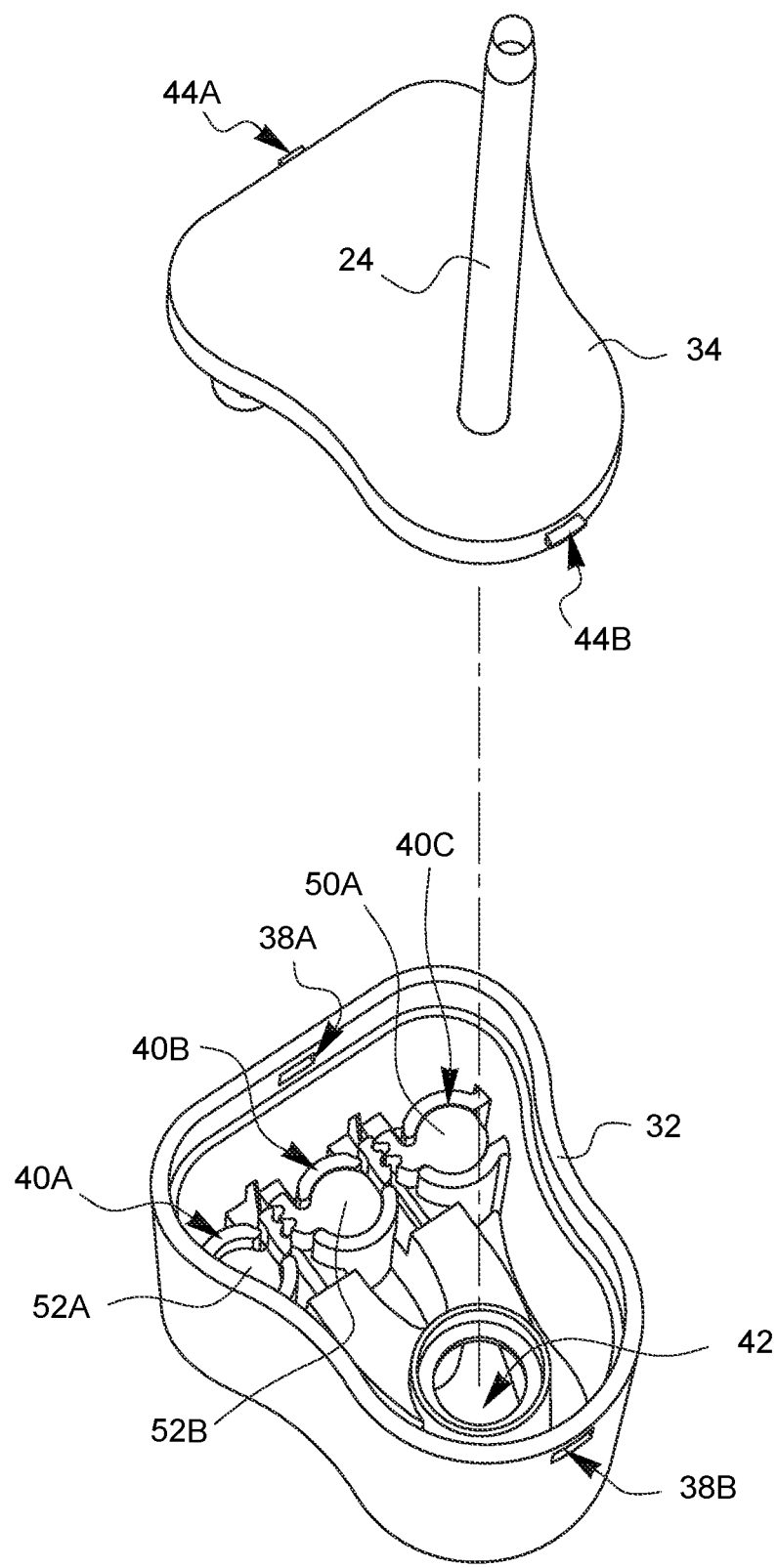

As shown in FIG. 4C, the resultant assembly of FIG. 4B has been turned upside-down and is being aligned with and installed into the resultant assembly of FIG. 4A. The tabs 44A, 44B will be snapped into the tab receiving openings 38A, 38B. The opening 42 in the upper flange cover 32 is sized to communicate with the cannular channel opening in the proximal end of the cannular channel (not visible in this view). When attached to the upper flange cover 32, the lower flange 34 also is configured to keep the cam grips 52A, 52B, 50B (not easily visible in this view because it is partially beneath cam grip 52B), and 50A from falling out of cam pockets 40A, 40B, 40C.

Figure 4D:
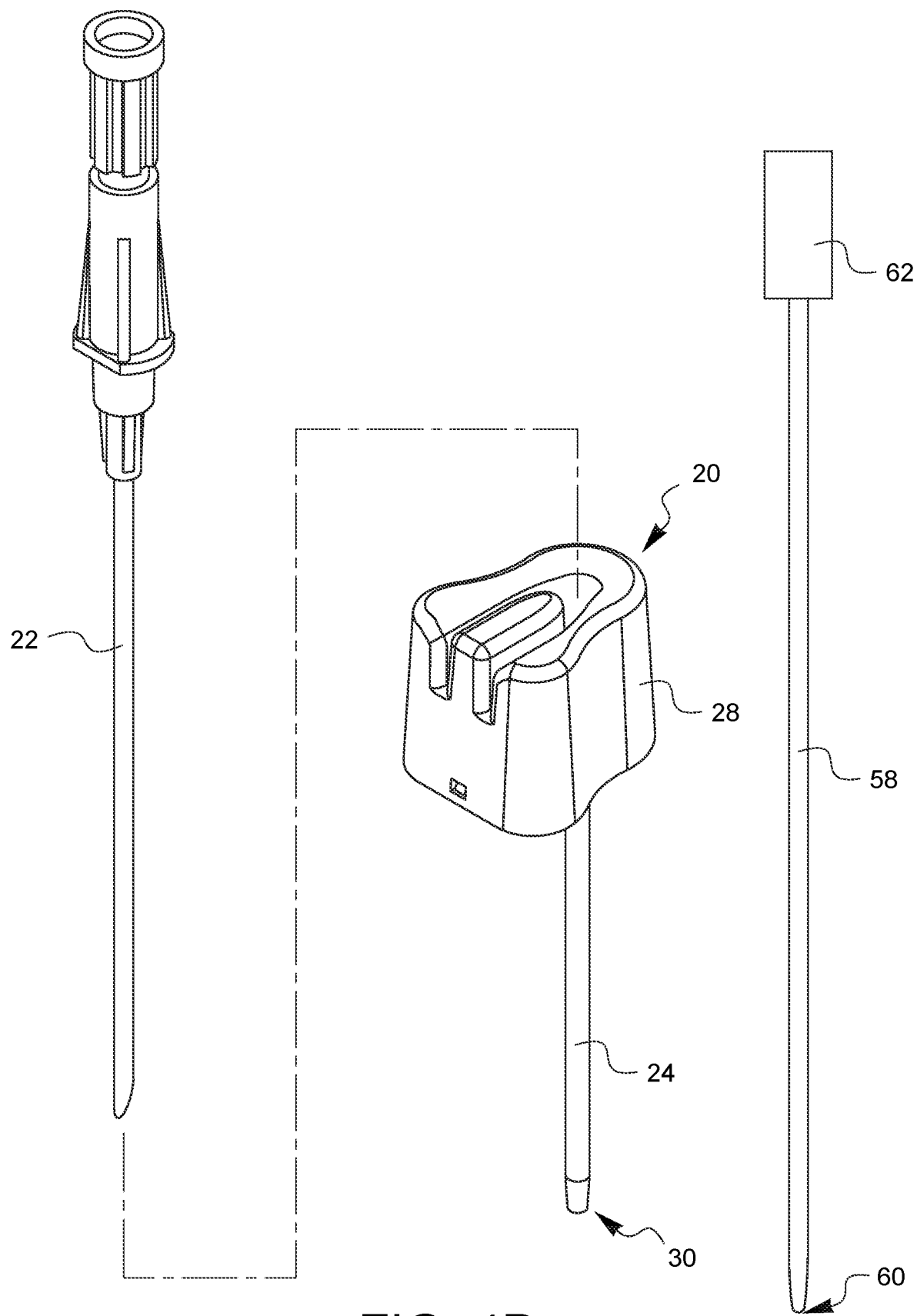

As shown in FIG. 4D, the needle 22 may be inserted into the cannular channel 24 of the fully assembled surgical port 20 through the opening in the flange 28. Alternatively, an obturator 58 may be inserted into the cannular channel 24. As discussed above, the obturator would have a blunt tip 60 which would be sized to extend past the distal end 30 of the cannular channel 24. The obturator 58 may also have a handle 62 for ease of use and to prevent the obturator 58 from passing all the way through the cannular channel 24 and into a patient.

Figure 5:
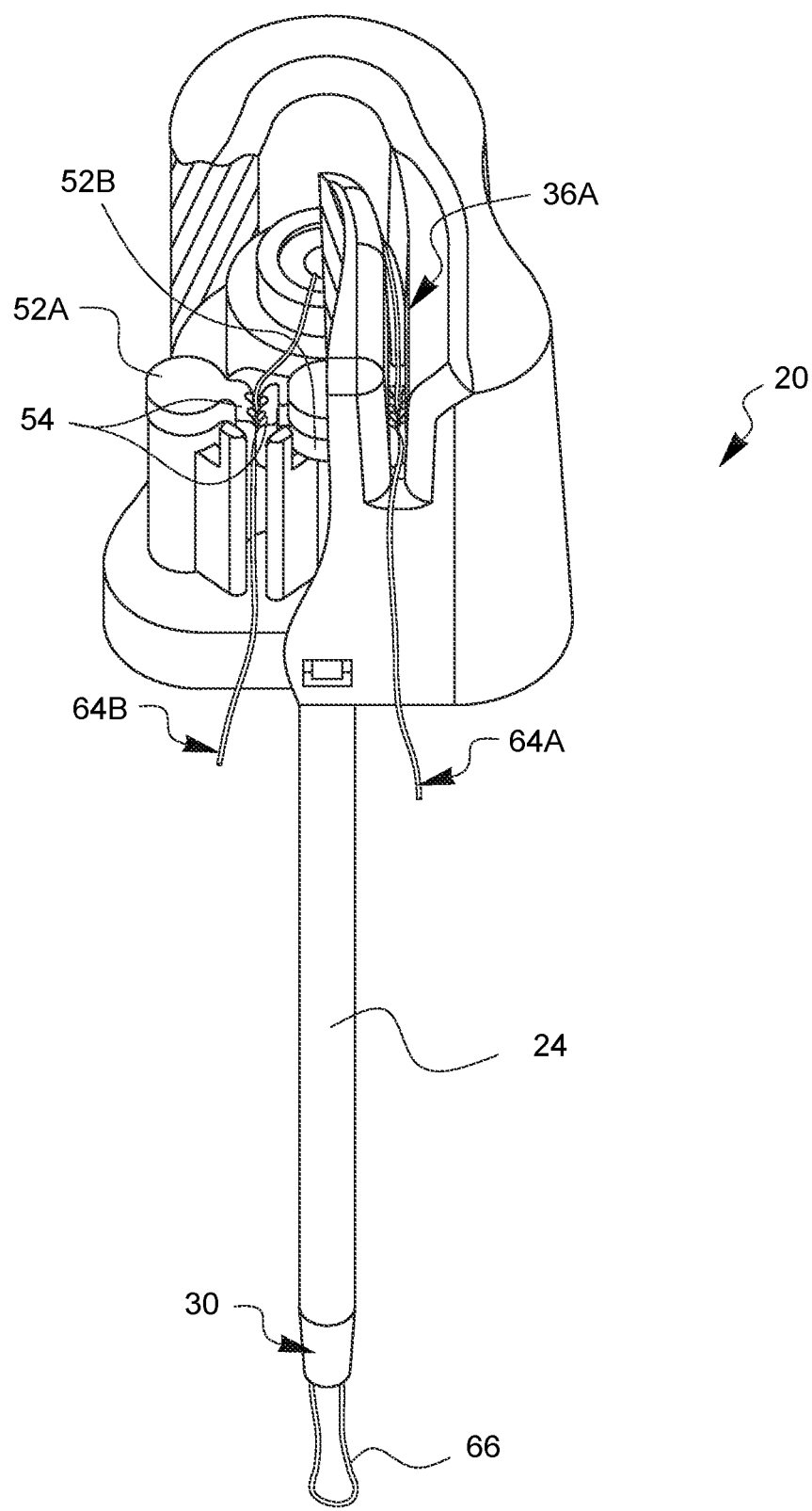
FIG. 5 is a partially exposed view of a surgical port through which the ends of a stay suture have been drawn.
Figure 6A:
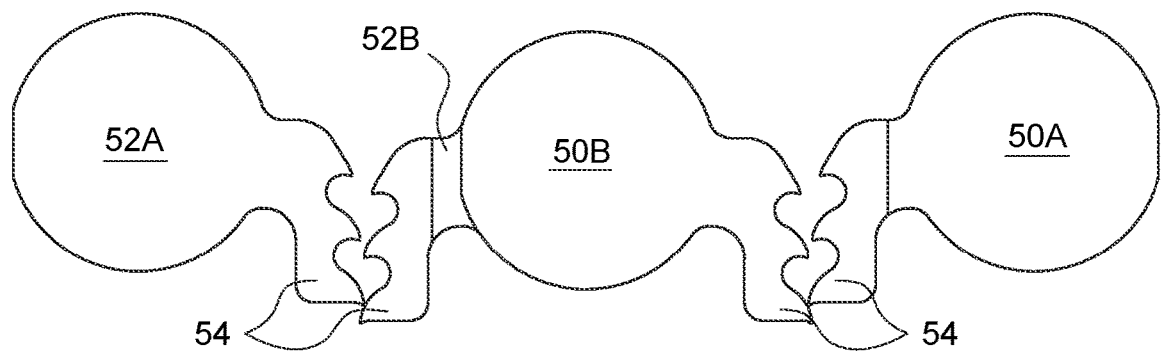
FIGS. 6A-6C illustrate operation of one embodiment of cam grips.
Figure 6B:
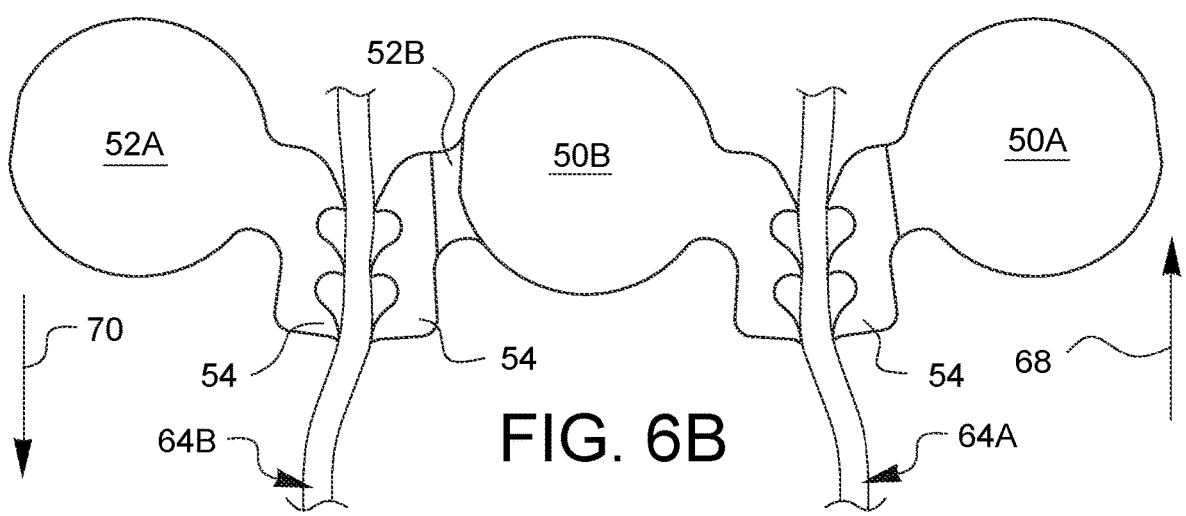
Figure 6C:
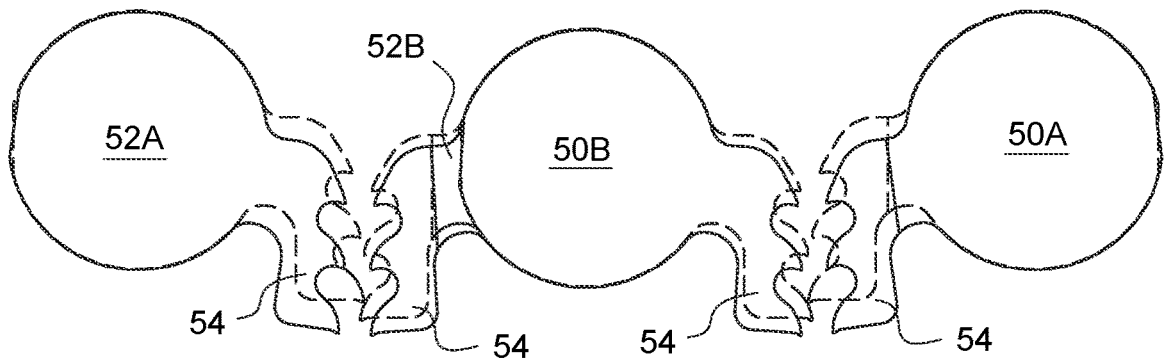

FIG. 5 is a partially exposed view of a surgical port 20 through which the ends 64A, 64B of a stay suture 66 have been drawn. This may be done by using a hook or a snare as described above. The stay suture 66 is shown looping out of the distal end 30 of the cannular channel 24 for simplicity, however, it should be understood that such a stay suture 66 would be stitched through a desired tissue when in actual use. The stay suture ends 64A, 64B are pulled up through the cannular channel 24 and then down into the suture slots 36A, 36B, respectively. Suture slot 36B is not visible in this partially exposed view, allowing us to see more clearly how the suture may be engaged with the cam grips 52A, 52B. In particular, it can be seen that the suture leading to suture end 64B has been drawn through the opposing gripping arms 54 of cam grips 52A, 52B. As schematically illustrated in FIGS. 6A-6C, the cam grips 52A, 52B, 50A, 50B are able to rotate slightly within a small range defined by the cam pocket and the cam stops (not shown in this view). The broken line positions in FIG. 6C illustrates one end of the range of motion, while the solid line positions in FIG. 6C illustrates the other end of the range of motion for the cam grips 52A, 52B, 50A, 50B. This motion allows suture 64A, 64B to be drawn in-between respective pairs of gripping arms 54. The gripping arms 54 are configured to resist motion of the suture 64A, 64B in a backwards direction 68 while allowing the suture to be pulled to a desired tension in a forwards direction 70. The opposing pairs of gripping arms 54 may be configured to hold a single suture or multiple suture strands. In this way, stay sutures snared or hooked back through the surgical port 20 may be held in place by pulling the suture ends down into one or more suture slots 36A, 36B. The gripping arms 54 will hold the suture at the set tension.

Figure 7:
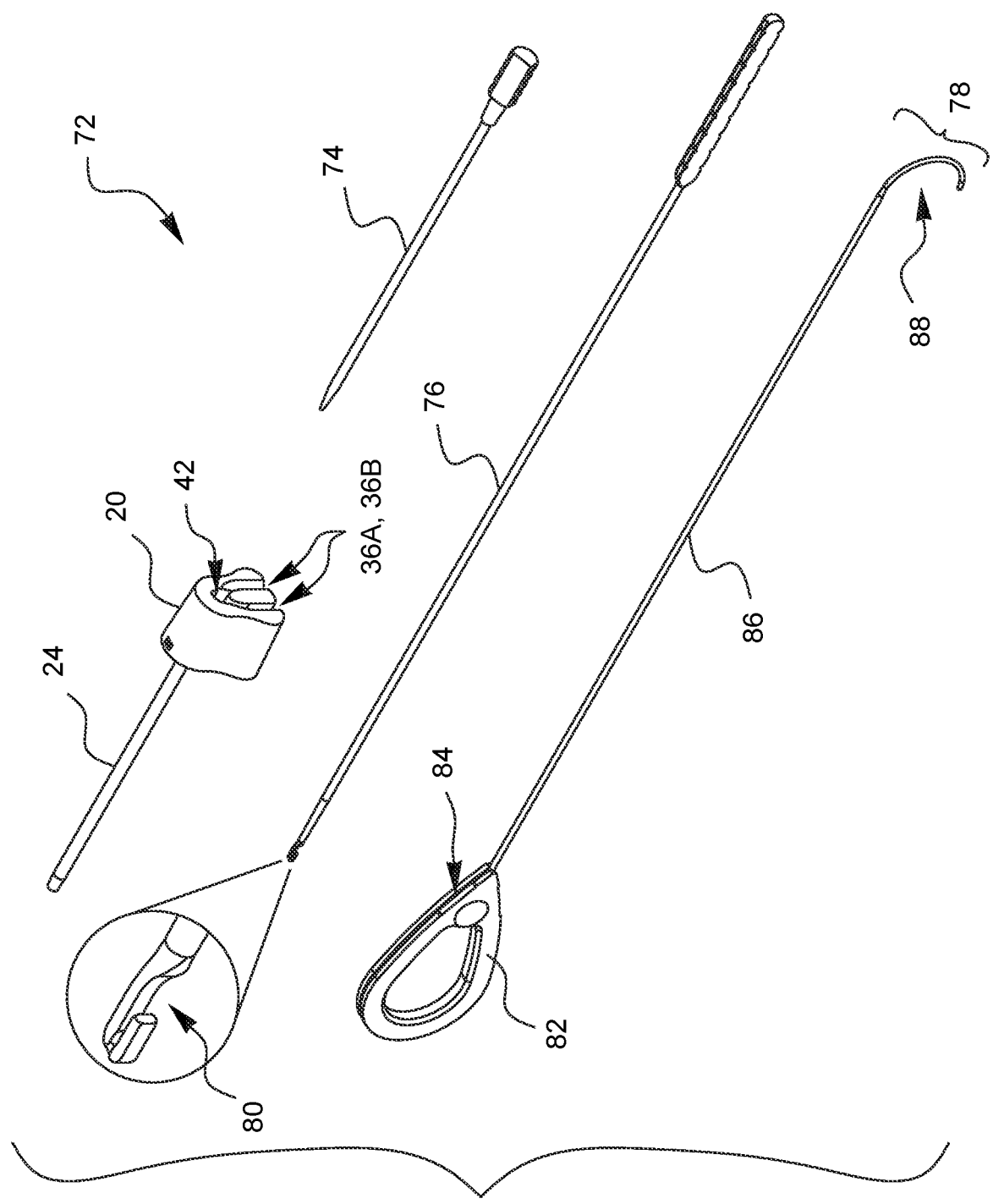
FIG. 7 illustrates one embodiment of a surgical port system.

FIG. 7 illustrates one embodiment of a surgical port system 72. The system 72 has a surgical port 20, an obturator 74, a hook 76 device, and a snare device 78. The surgical port 20 has a flexible cannular channel 24 in this embodiment. The obturator 74 may be placed into the opening 42 of the surgical port 20 to enable the enable the flexible cannular channel 24 to be passed through tissue exposed by a small skin incision. The obturator 74 may then be removed from the surgical port 20 and either the hook device 76 or the snare device 78 may be placed into the opening 42 for capturing the ends of a stay suture and pulling them out of the surgical port 20. The hook device 76 has a distal hook 80 with an atraumatic tip for grabbing the desired suture. The snare device 78 has a plastic target 82 at its distal end. The plastic target 82 is held by a snare loop 84 (not easily visible in FIG. 7, but visible in FIG. 10A). The snare loop 84 extends through a metal tube 86 where it is coupled to a curved metal handle 88. The plastic target 82 can be removed from the snare device 78 to expose the snare loop 84. The snare loop 84 and the end of the metal tube 86 near the snare loop 84 may be placed into the opening 42 and through the flexible cannular channel 24 of the surgical port 20. A desired suture can be placed through the snare loop 84, and the curved metal handle 88 and metal tube 86 can be simultaneously pulled away from the surgical port 20 to draw the suture in the snare loop 84 out of the opening 42. The stay suture ends may be tensioned as desired and then pulled into suture slots 36A, 36B of the surgical port 20. Each suture slot 36A, 36B can hold a pair of suture ends as described above, so each surgical port 20 may be used with at least two stay sutures.

Figure 8A:
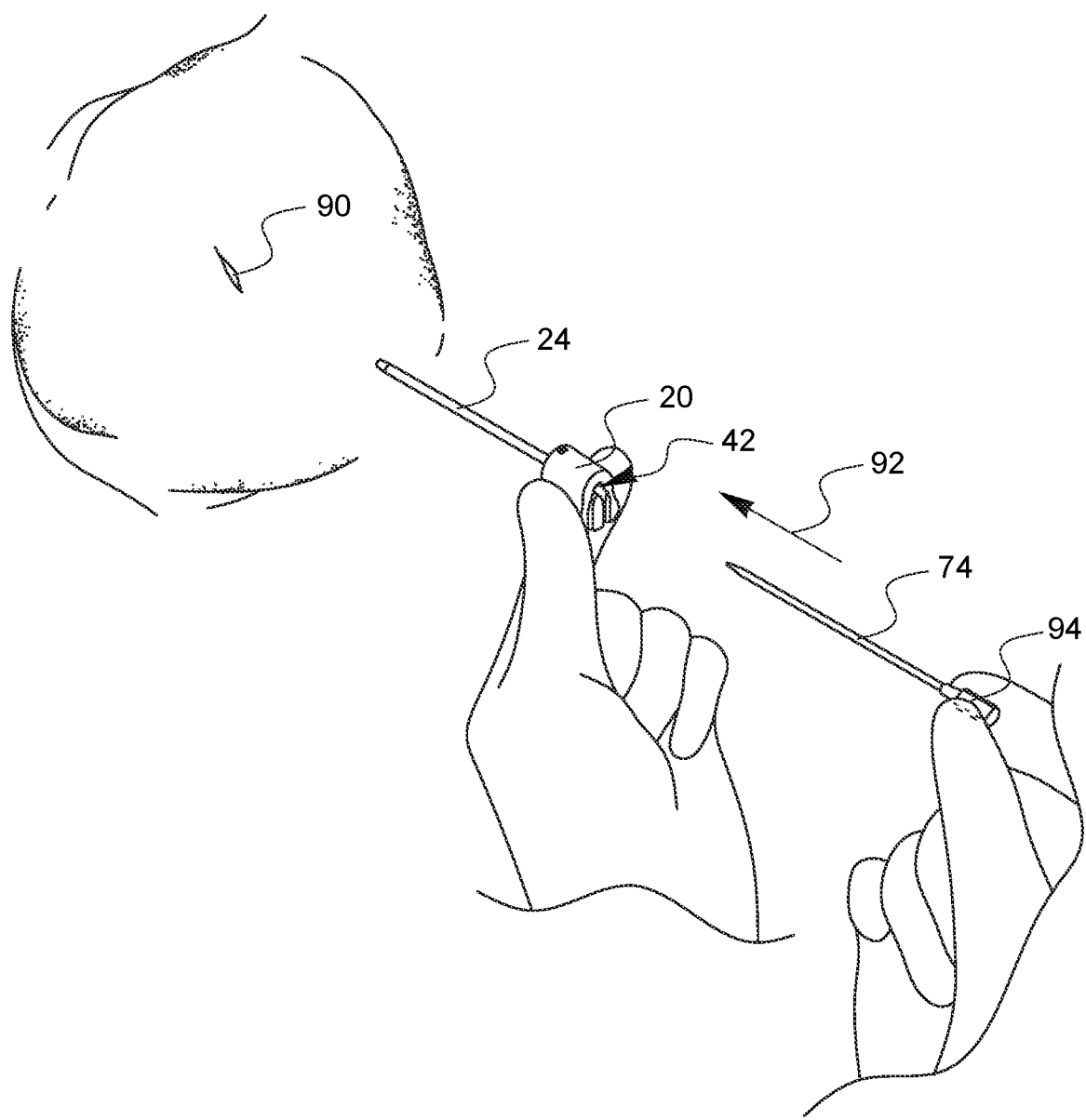
FIGS. 8A-8E illustrate one embodiment of a method for installing the surgical port of FIG. 7 in a patient.
Figure 8B:
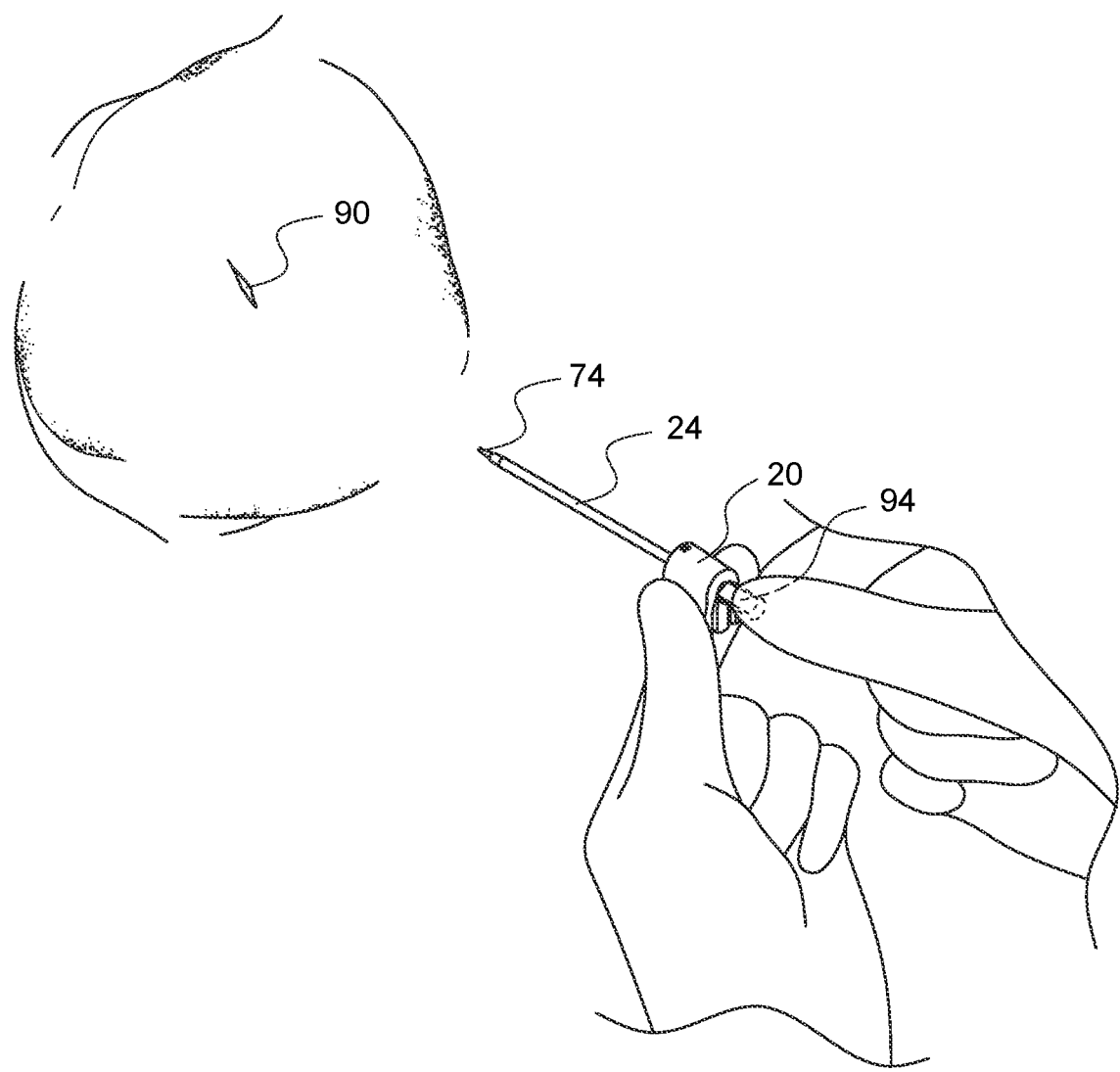
Figure 8C:
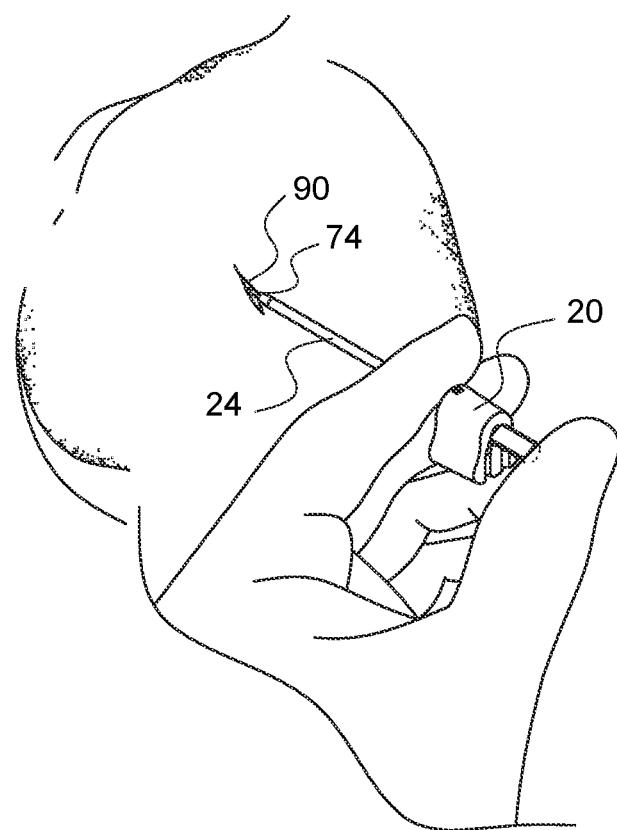
Figure 8D:
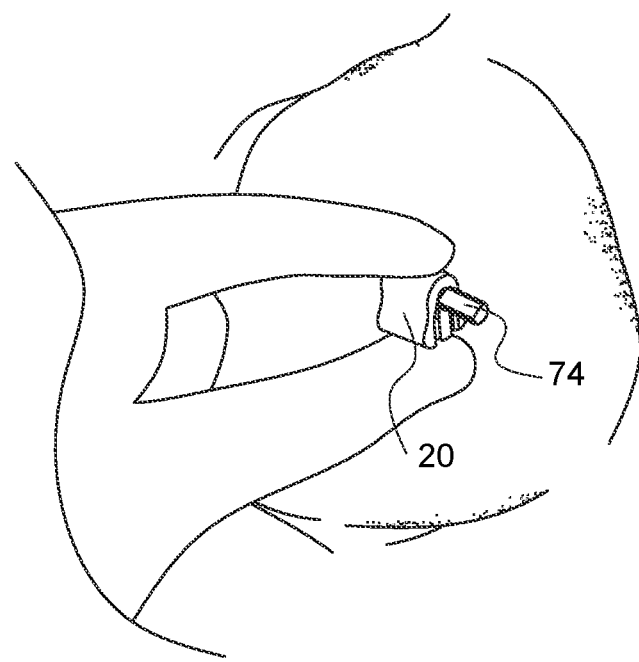
Figure 8E:
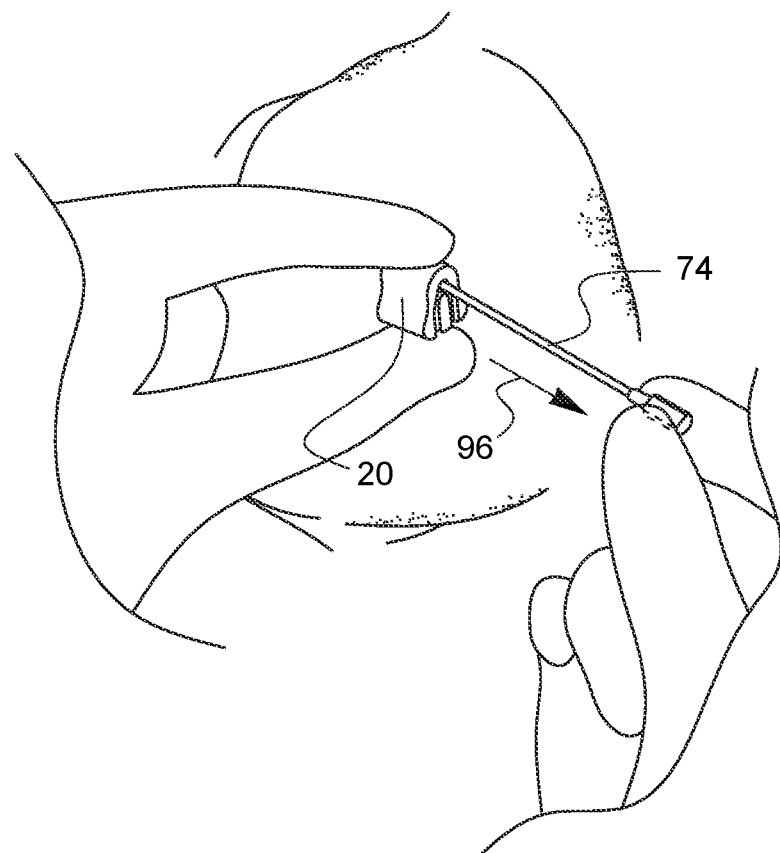

FIGS. 8A-8E illustrate one embodiment of a method for installing the surgical port of FIG. 7 in a patient. As illustrated in FIG. 8A, a small skin incision 90 is opened at a desired location on a patient for stay suture passage based on a surgeon's preference and experience. The obturator 74 is aligned with the opening 42 on the surgical port 20 and then placed 92 into the opening 42 until the handle 94 of the obturator 74 contacts the surgical port 20 as shown in FIG. 8B. As shown in FIG. 8C, the obturator 74 and cannular channel 24 of the surgical port 20 are inserted through the incision 90. The obturator 74 can be worked carefully through the underlying tissue, taking care to avoid location of known blood vessels, nerves, and other sensitive structures and organs, until the surgical port 20 contacts the patient as shown in FIG. 8D. As shown in FIG. 8E, the obturator 74 may be removed 96 while the surgical port 20 is held against the patient.

Figure 9A:
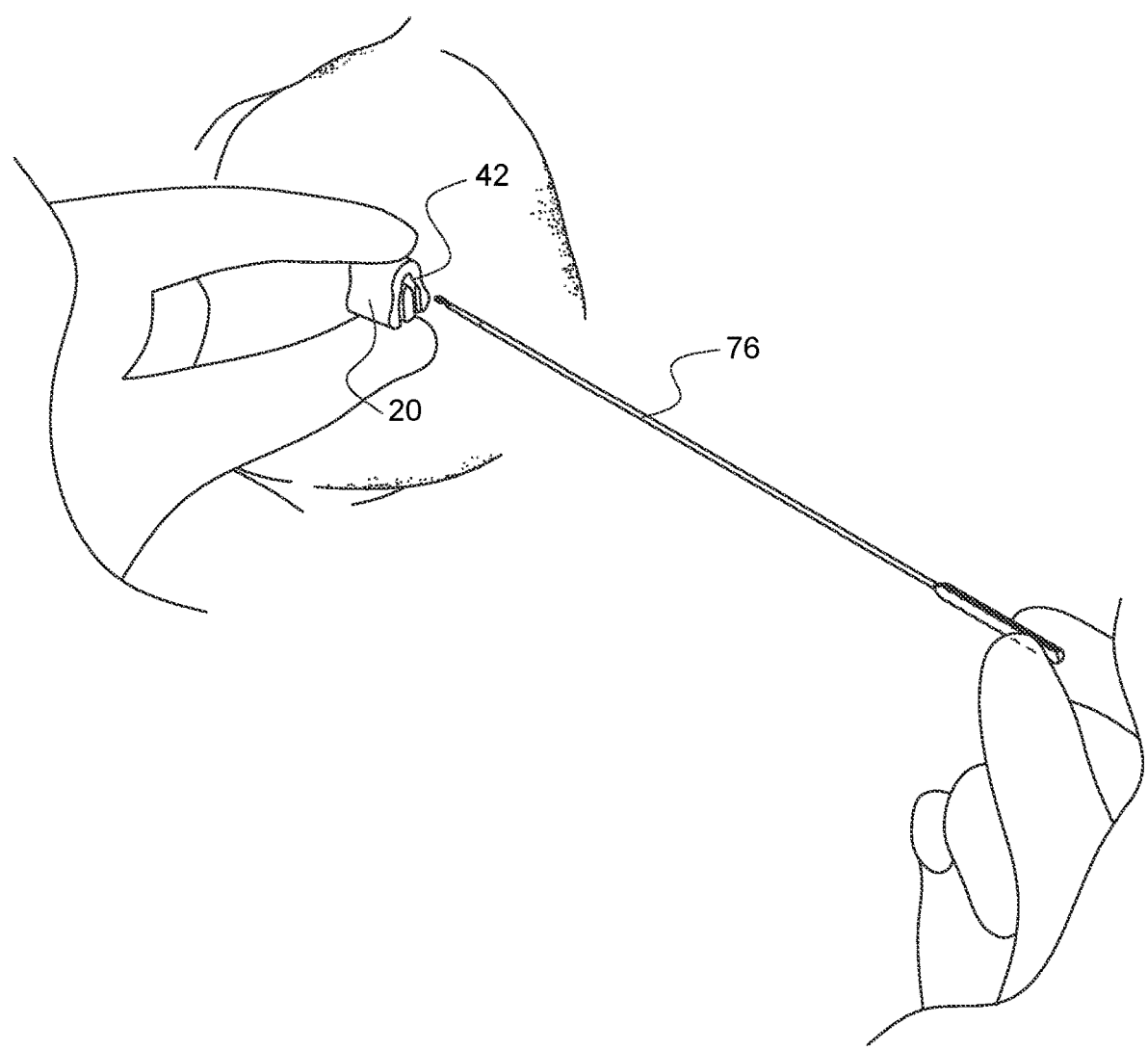
FIGS. 9A-9F illustrate one embodiment of a method for pulling a stay suture through the surgical port of FIG. 7 using the hook of FIG. 7.
Figure 9B:
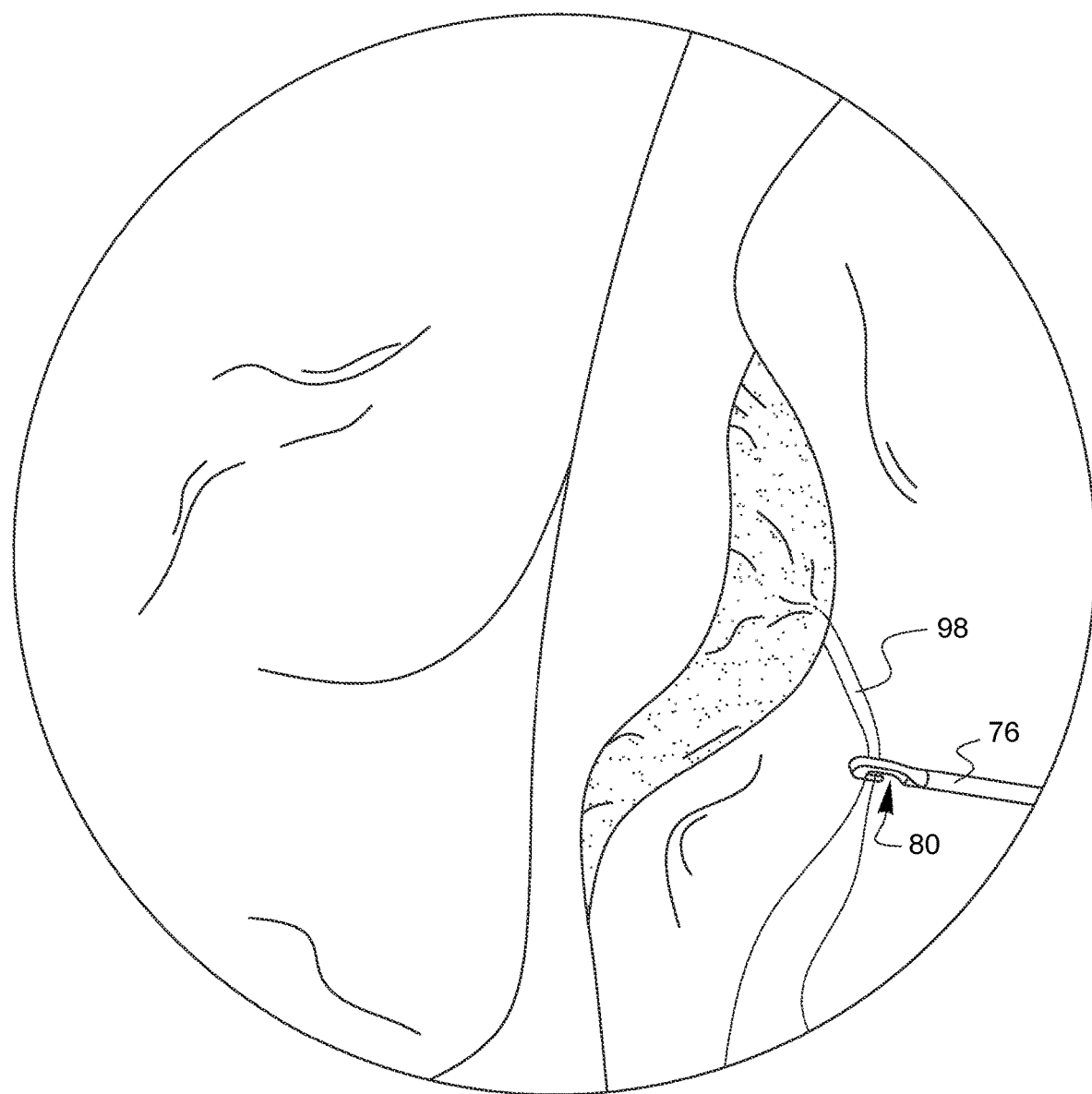
Figure 9C:
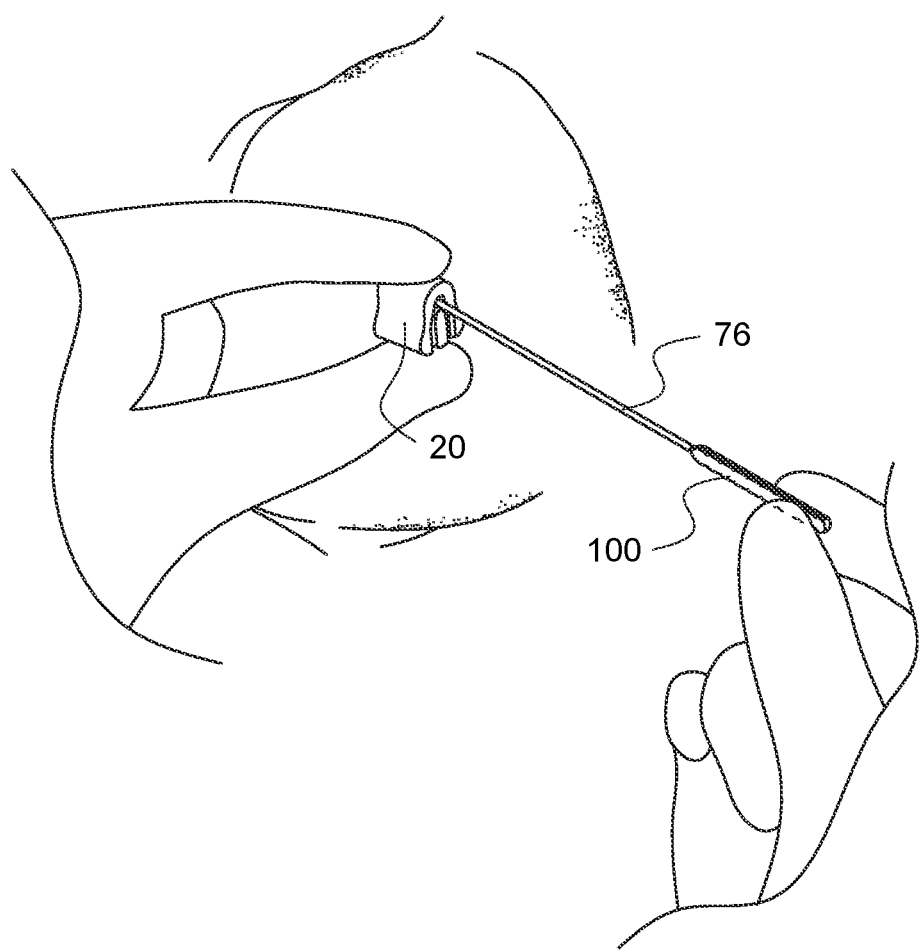
Figure 9D:
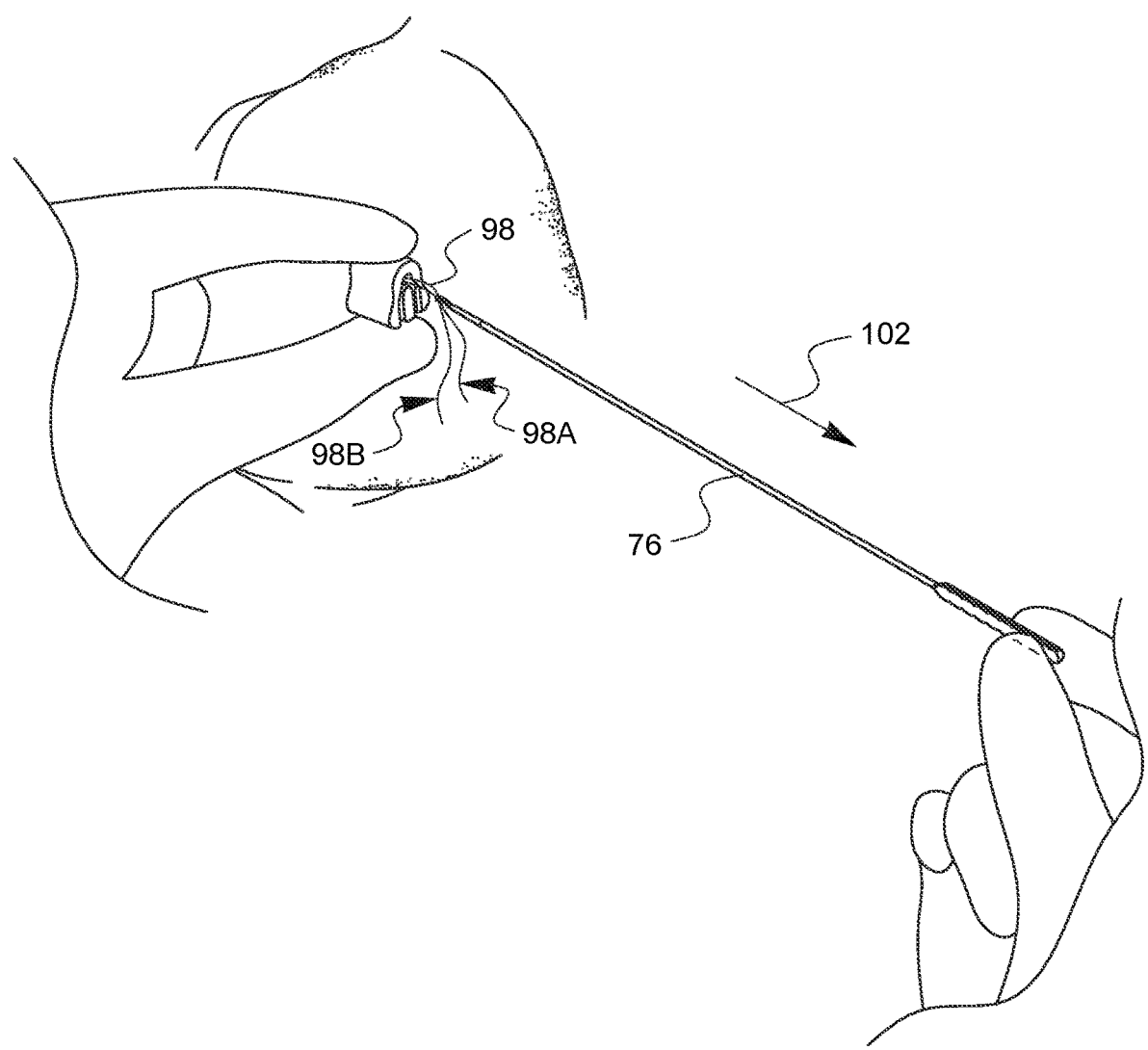
Figure 9E:
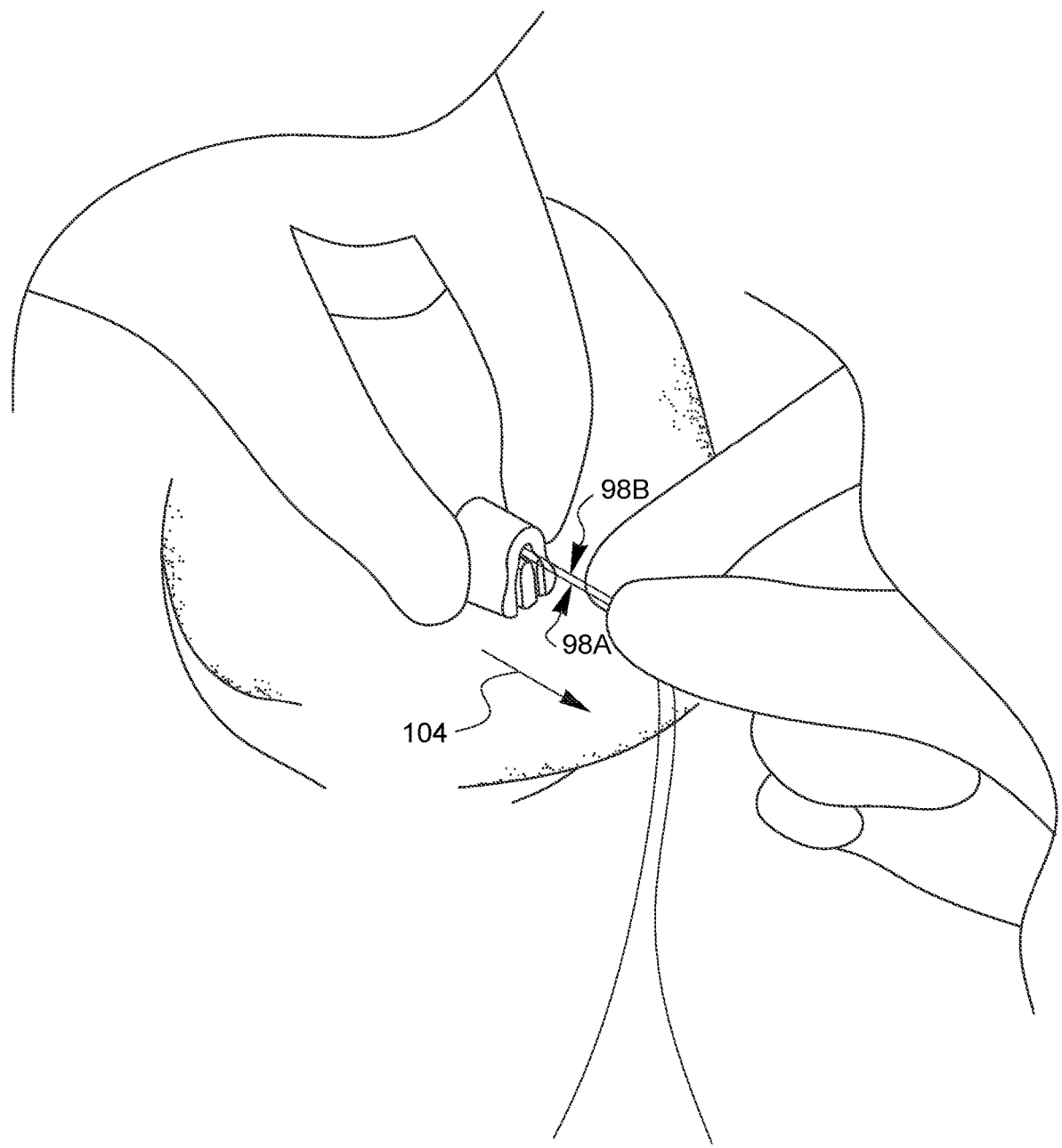
Figure 9F:
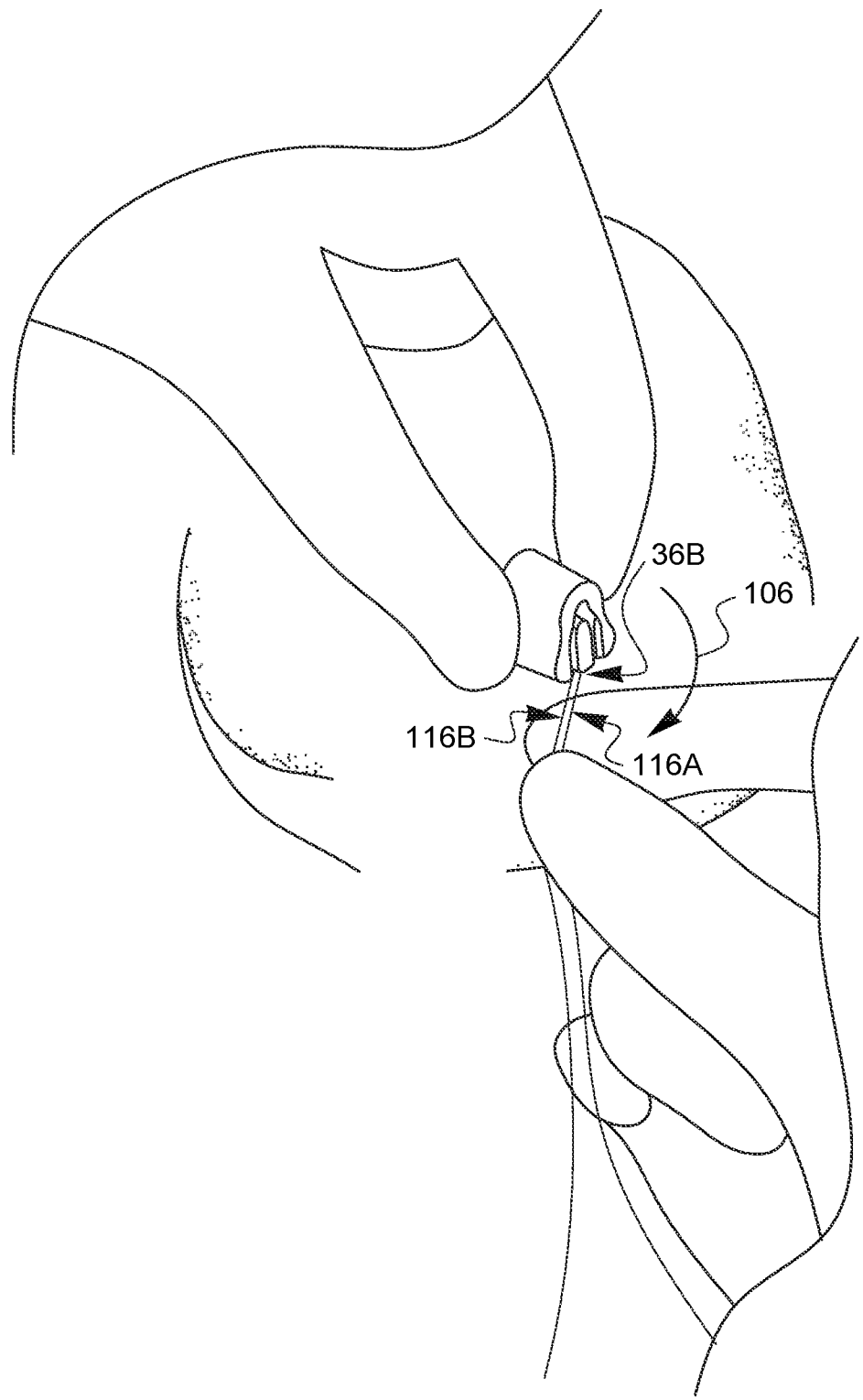

FIGS. 9A-9F illustrate one embodiment of a method for pulling a stay suture through the installed surgical port 20 using the hook device 76. The distal end of the hook device 76 may be inserted into the opening 42 of the surgical port 20 as shown in FIG. 9A. As illustrated in the simulated endoscopic visualization view of FIG. 9B, one or both strands of the desired stay suture 98 may be captured within the distal hook 80 of hook device 76 by manipulating the proximal handle 100 of the hook device 76 outside of the patient as shown in FIG. 9C. As shown in FIG. 9D, the hook device 76 may then be pulled 102 out of the patient while steadying the surgical port 20 to bring the stay suture 98 ends 98A, 98B out of the surgical port 20. As shown in FIG. 9E, the stay suture ends 98A, 98B can be tensioned 104 per surgeon's discretion to position the tissue held by the stay suture 98 as desired. As shown in FIG. 9F, the stay suture ends 98A, 98B can be locked to maintain the desired tension by pulling 106 them down into one of the suture slots 36B.

Figure 10A:
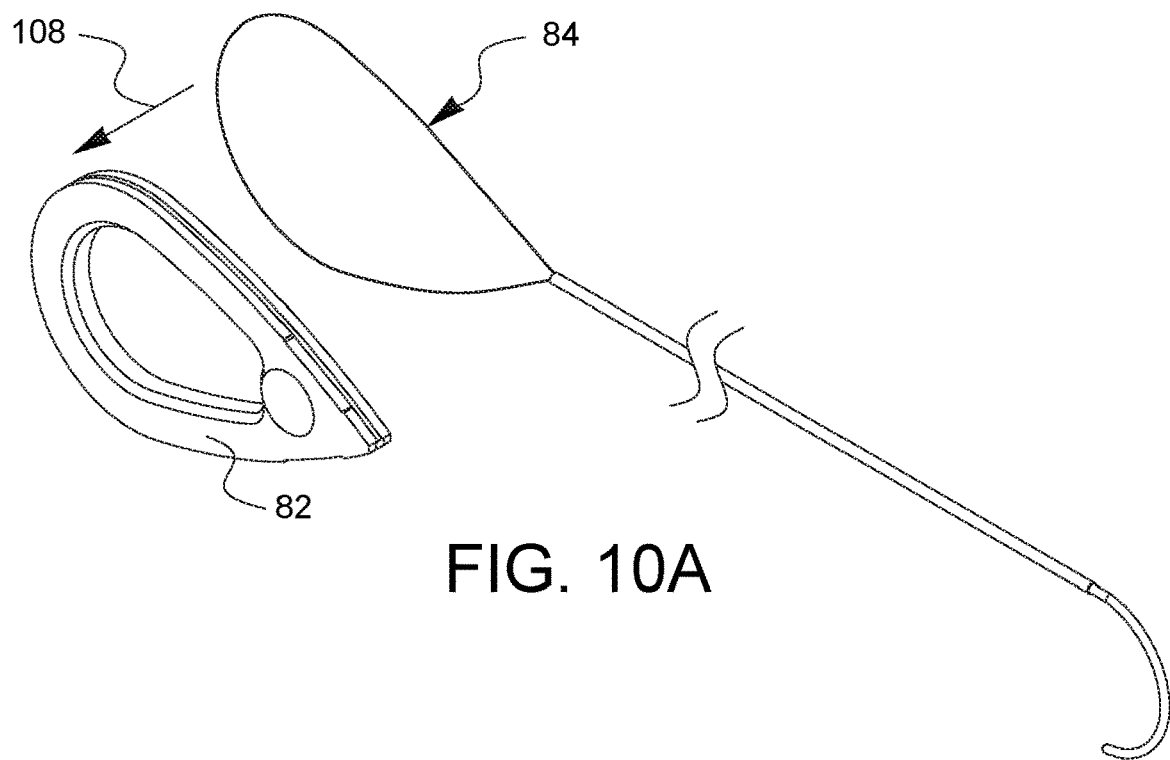
FIGS. 10A-10J illustrate one embodiment of a method for pulling a stay suture through the surgical port of FIG. 7 using the snare of FIG. 7
Figure 10B:
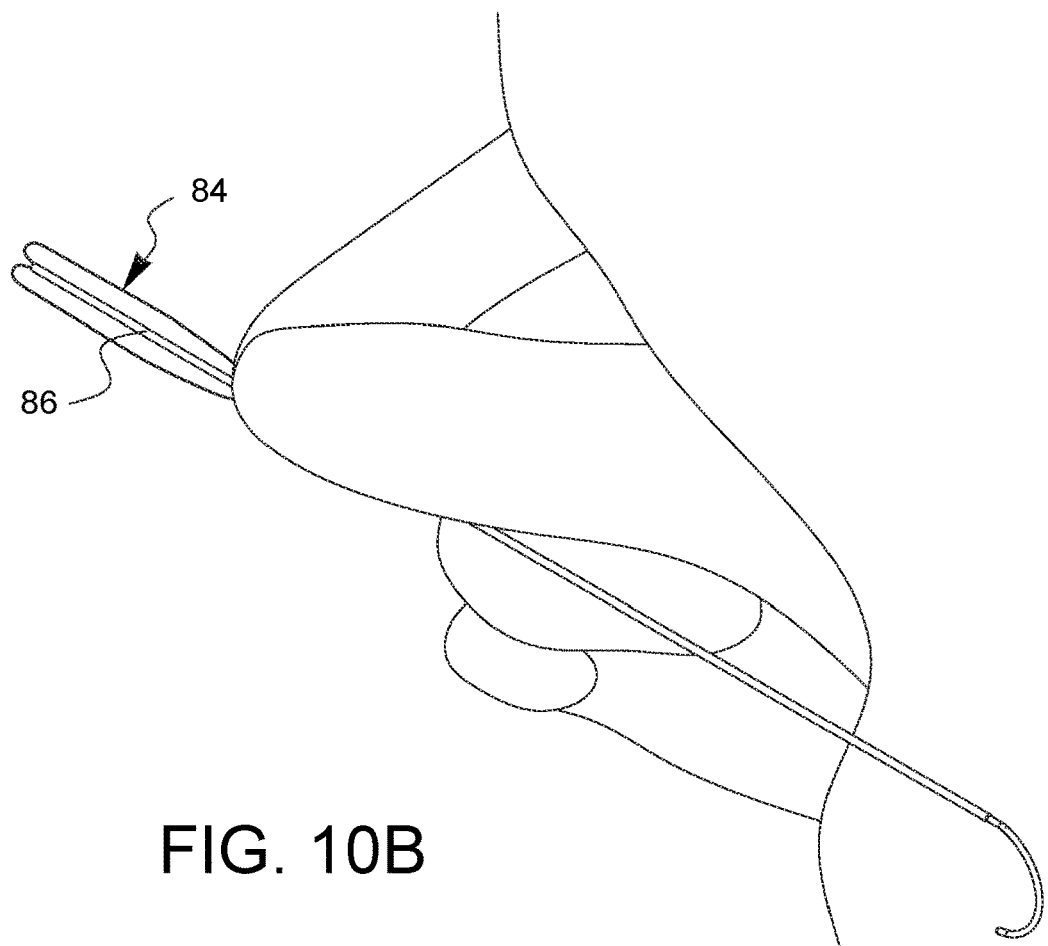
Figure 10C:
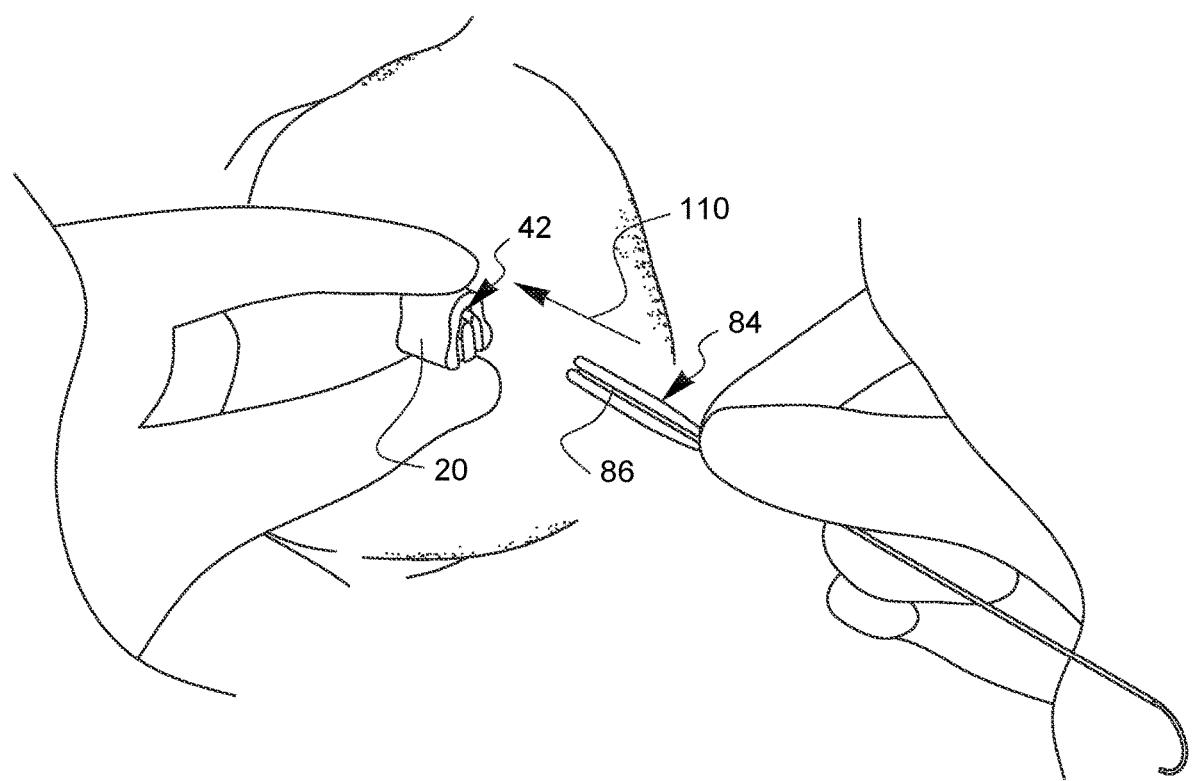
Figure 10D:
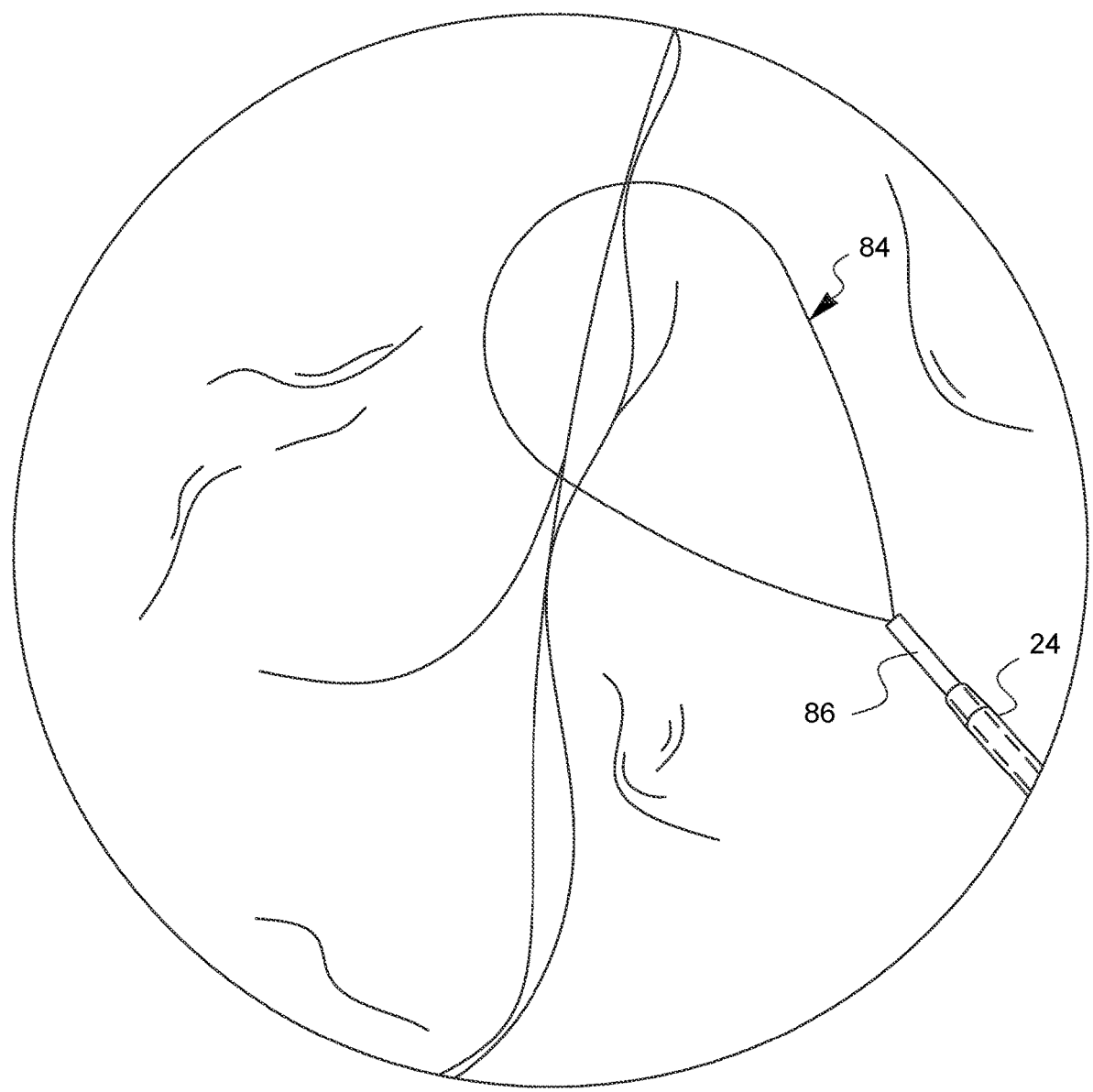
Figure 10E:
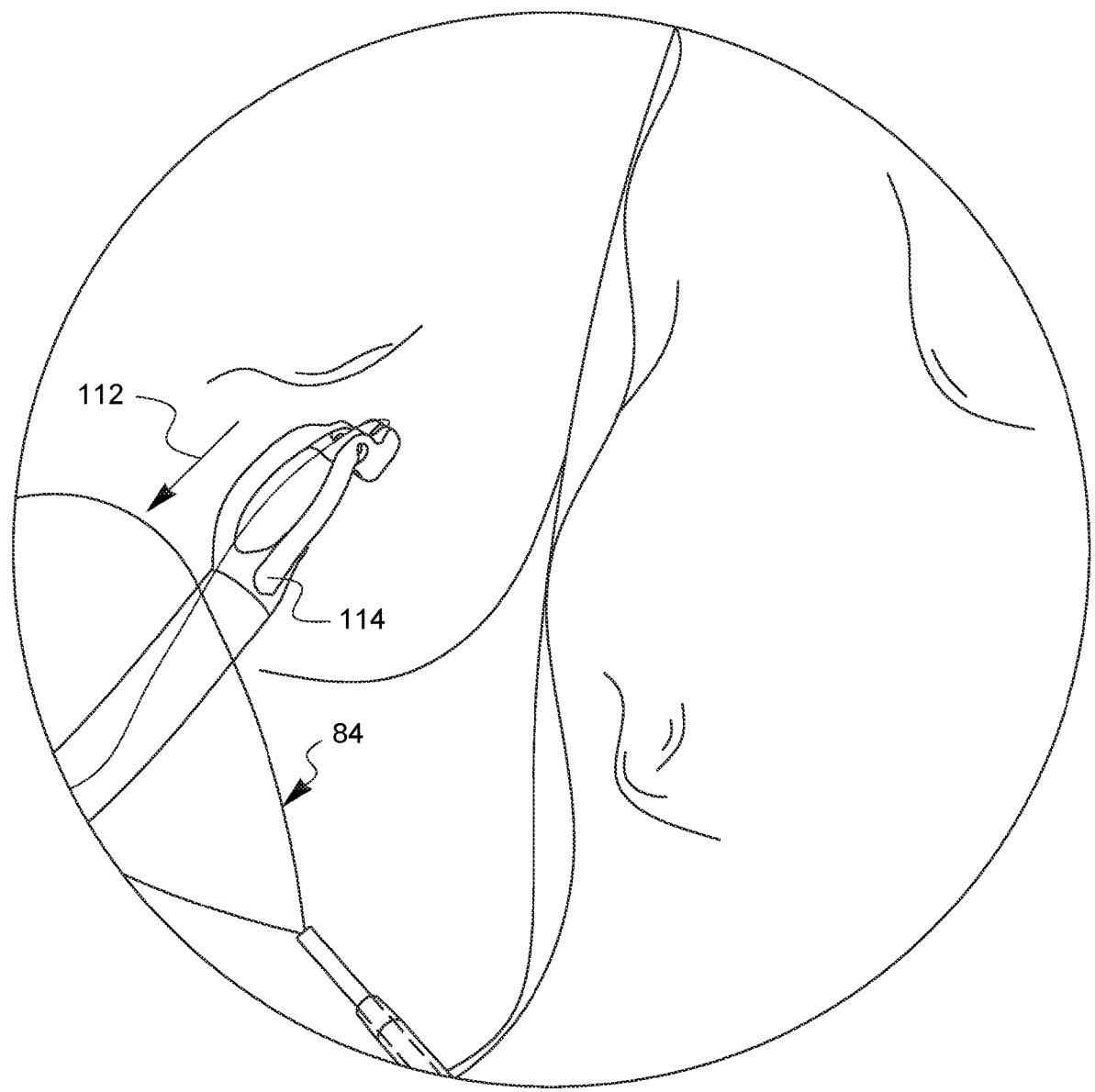
Figure 10F:
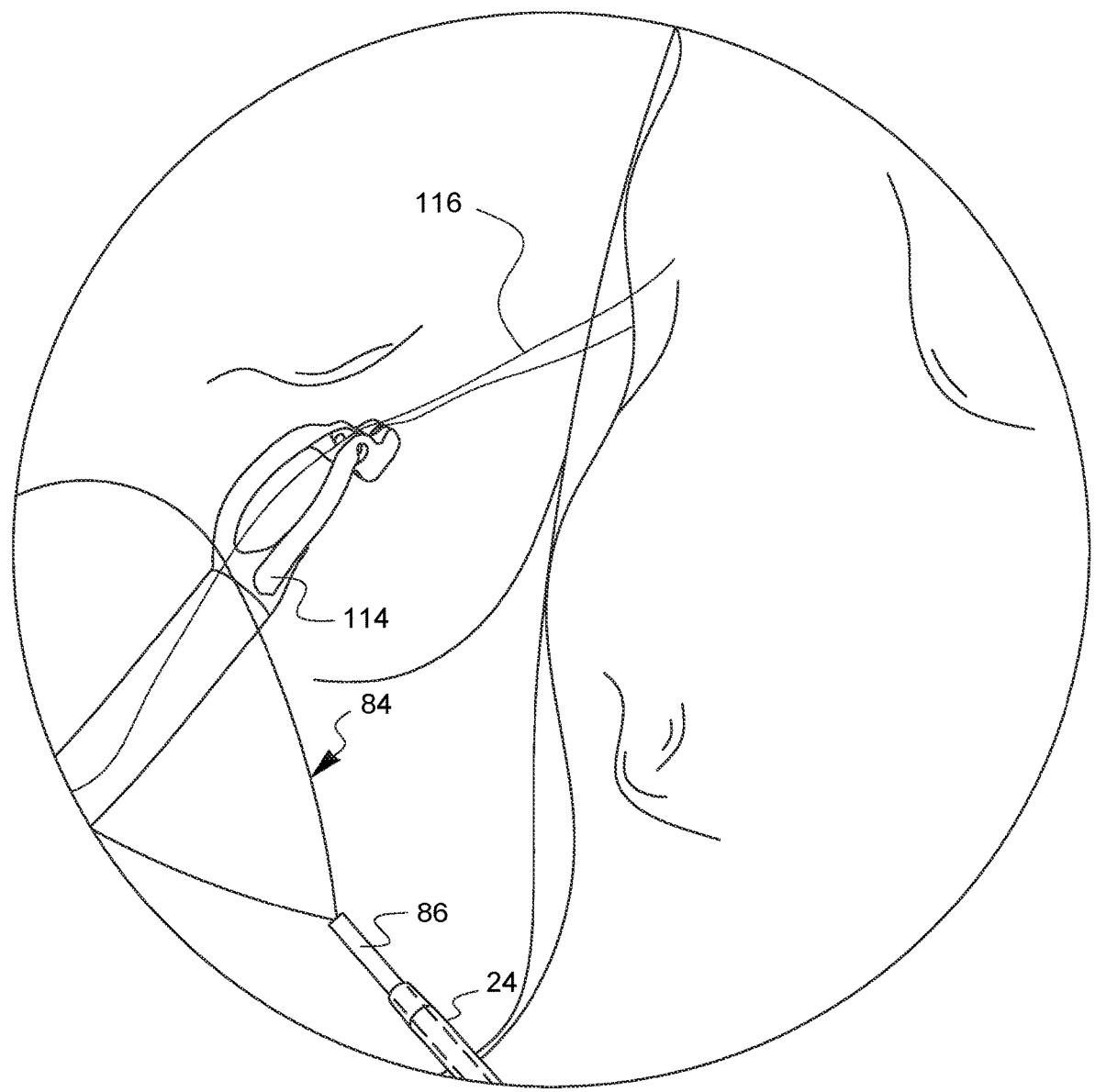
Figure 10G:
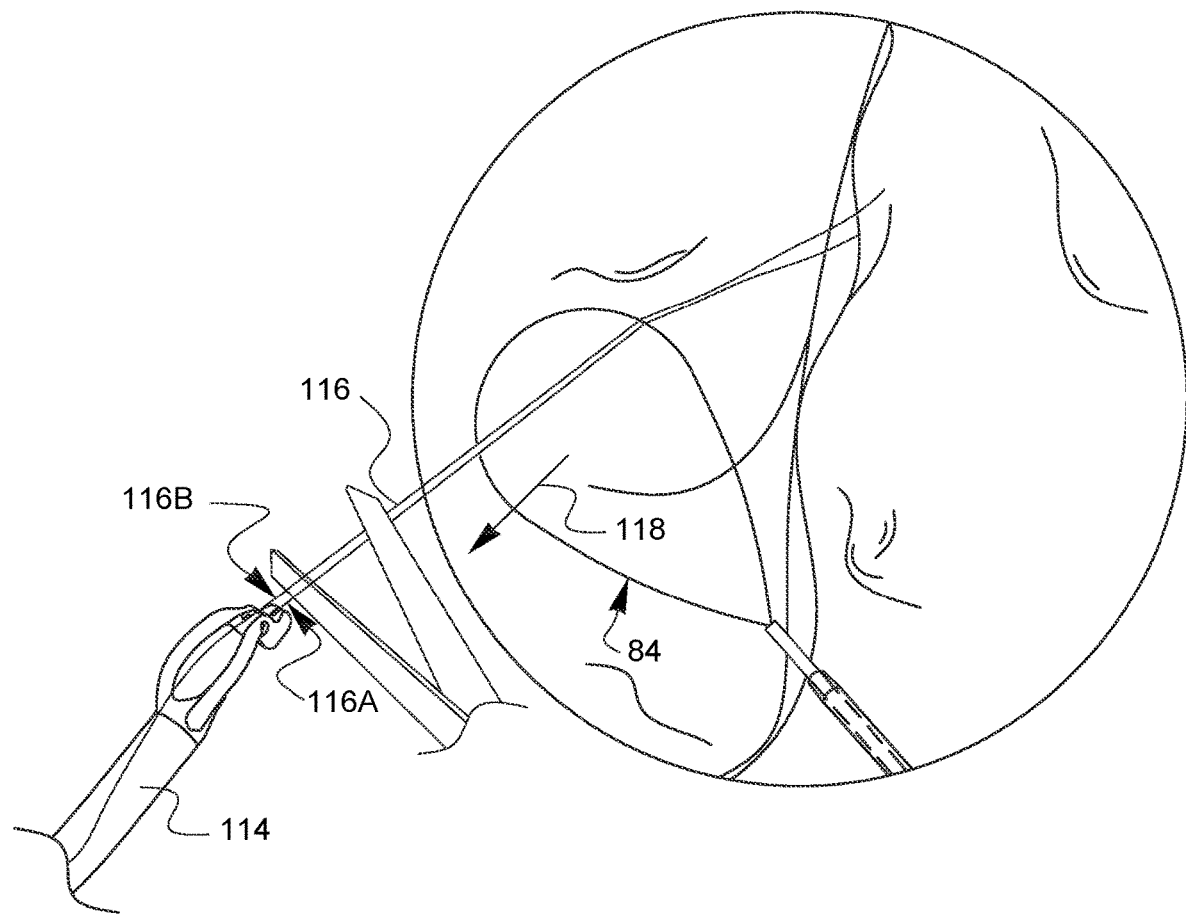
Figure 10H:
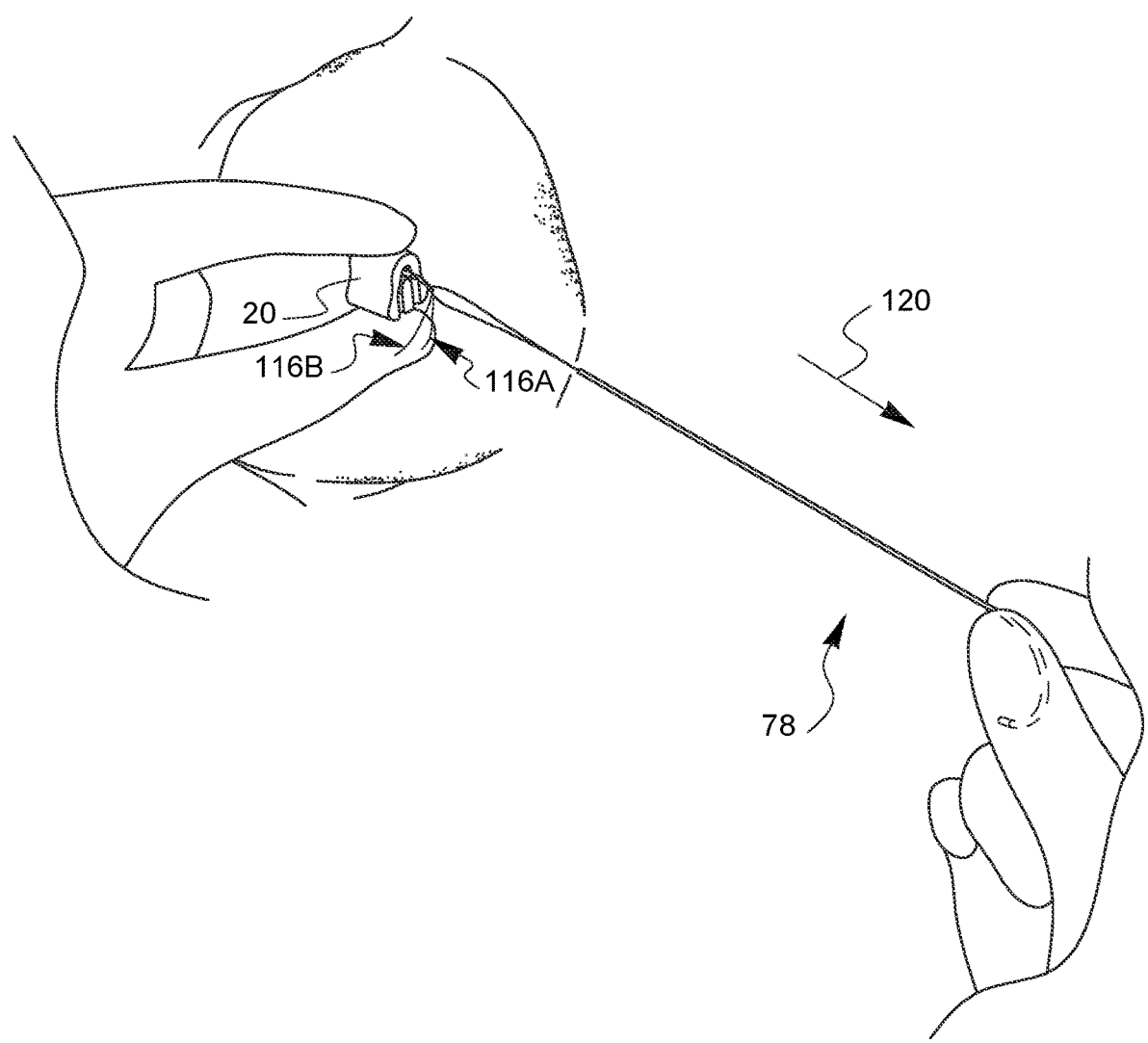
Figure 10:
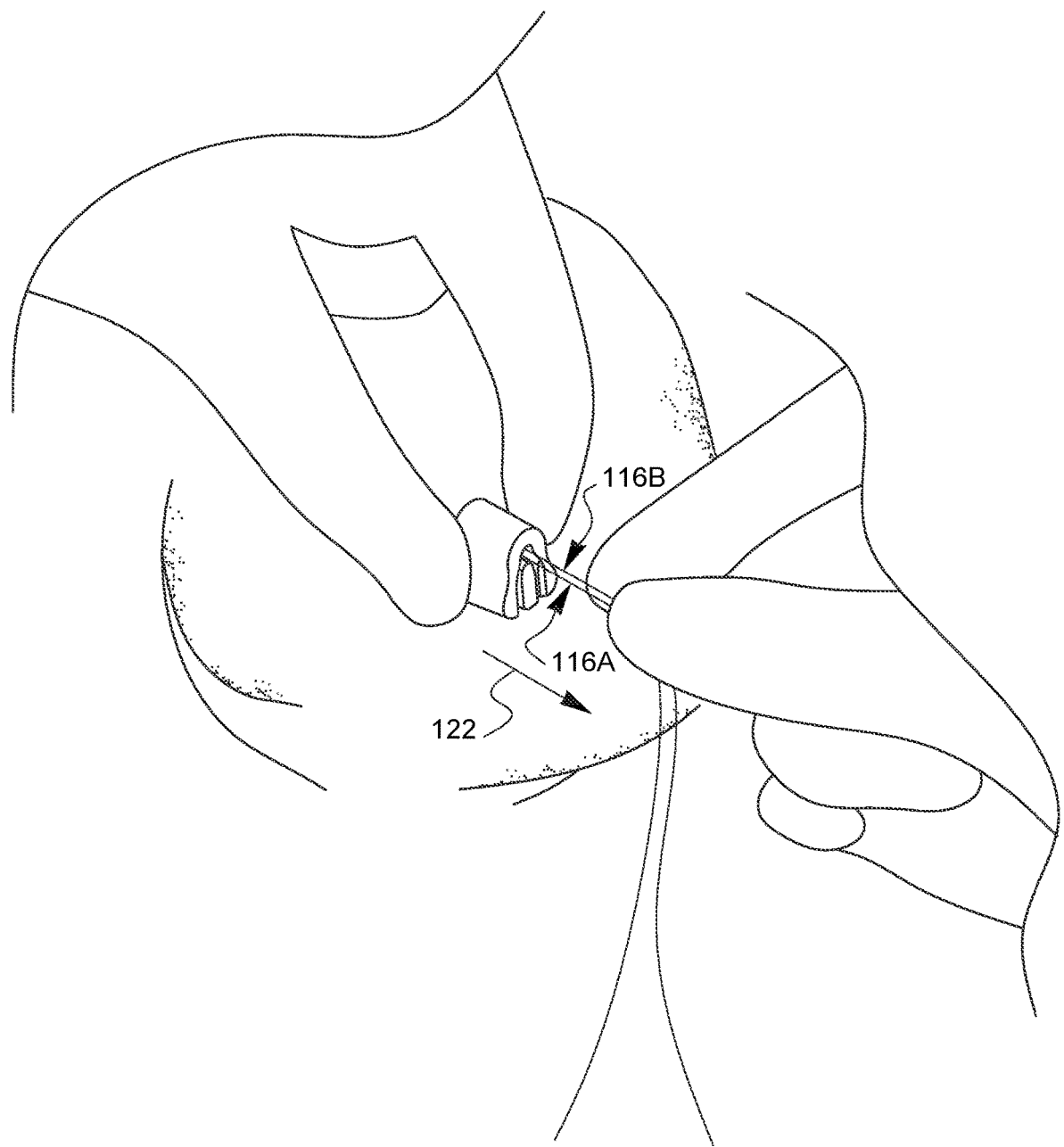
Figure 10J:
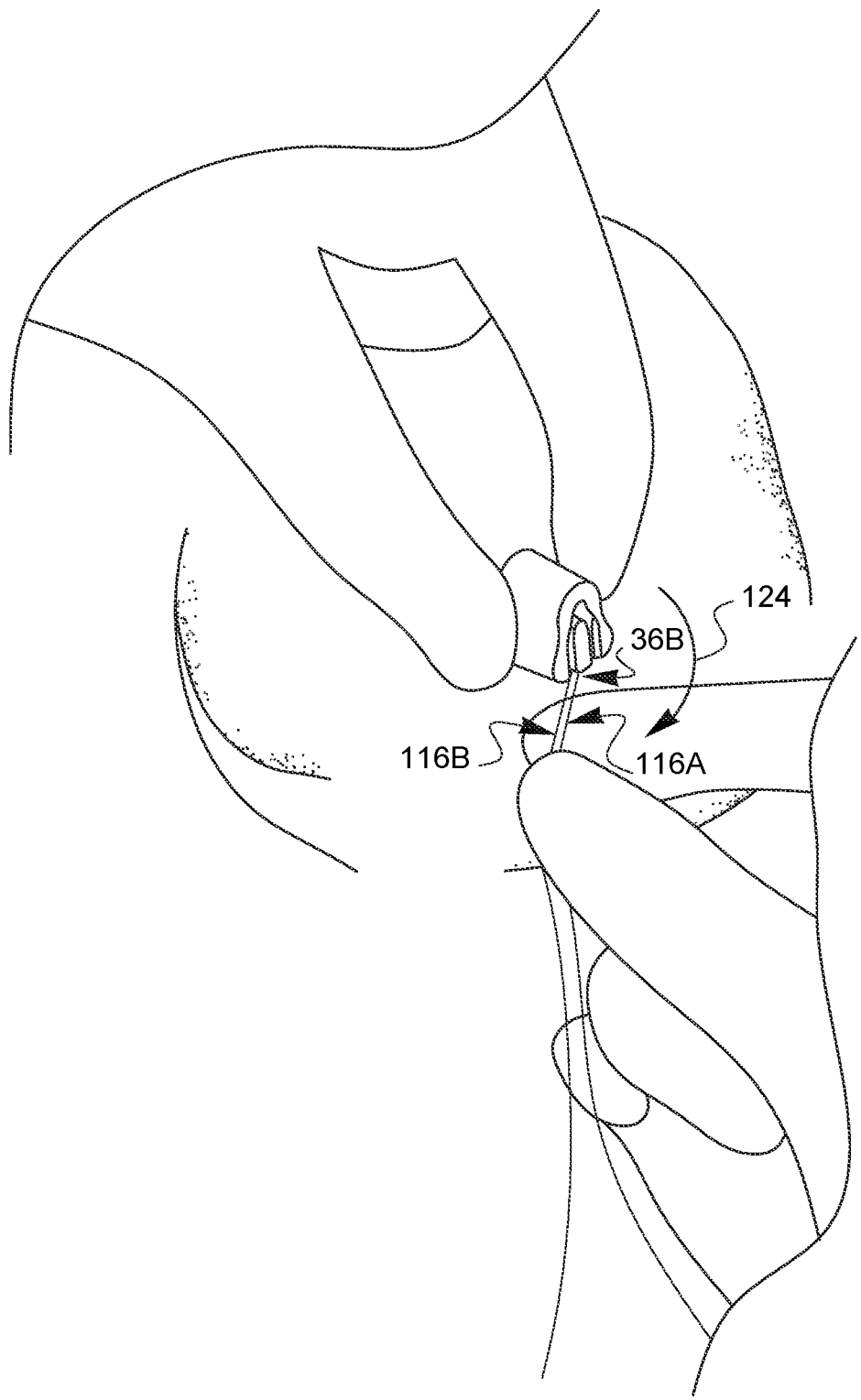

FIGS. 10A-10J illustrate one embodiment of a method for pulling a stay suture through the surgical port of FIG. 7 using the snare device 78. As shown in FIG. 10A, the plastic target 82 may be pushed 108 out of the snare loop 84. As shown in FIG. 10B, the snare loop 84 may be folded back against the tube 86 of the snare device. As illustrated in FIG. 10C, the folded loop 84 end of the snare device may be inserted 110 into the opening 42 of the surgical port 20. The tube 86 should be inserted far enough through the cannular channel for the snare loop 84 to exit the cannular channel 24 inside the patient as shown in the simulated endoscopic visualization view of FIG. 10D. As illustrated in the simulated endoscopic visualization view of FIG. 10E, the snare loop 84 may be placed over the sewing end of a suturing device 114 inside the patient. The suturing device 114 may be an automated suturing device or a needle grasping device. As illustrated in FIG. 10F, a stay suture 116 may be sewn into a desired suture location using the suturing device 114. As schematically shown in FIG. 10G, the suturing device 114 may be withdrawn 118 back through the snare loop 84 (thereby pulling the stay suture through the snare loop 84) and, outside of the patient, the stay suture ends 116A, 116B may be cut to separate them from the suturing device 114 or any needle caps or needles to which they might be attached. As shown in FIG. 10H, the snare device 78 may be pulled 120 out of the patient while steadying the surgical port 20 to bring the stay suture ends 116A, 116B out of the surgical port 20. As shown in FIG. 10I, the stay suture ends 116A, 116B can be tensioned 122 per surgeon's discretion to position the tissue held by the stay suture 116 as desired. As shown in FIG. 10J, the stay suture ends 116A, 116B can be locked to maintain the desired tension by pulling 124 them down into one of the suture slots 36B.

Various advantages of a surgical port for stay sutures have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An apparatus for suture management, the apparatus comprising:
   a first cam grip comprising:
      a first cam base at least partially defined by a perimeter edge; and
      a first cam gripping arm coupled to the first cam base, the first cam gripping arm having an edge portion comprising a first plurality of teeth,
      wherein the first cam grip is configured to rotate about a first rotational axis that extends through the first cam base,
   a second cam grip comprising:
      a second cam base at least partially defined by a perimeter edge; and
      a second cam gripping arm coupled to the second cam base, the second cam gripping arm comprising an edge portion having a second plurality of teeth,
      wherein the second cam grip is configured to rotate about a second rotational axis that extends through the second cam base,
      wherein the first cam grip is oriented such that the first plurality of teeth is adapted to engage a first portion of a first segment of suture when the first segment of suture is displaced in a first direction and the second cam grip is oriented such that the second plurality of teeth is adapted to engage a second portion of the first segment of suture when the first segment of suture is displaced in the first direction, wherein the engagement of the first plurality of teeth with the first portion of the first segment of suture and the engagement of the second plurality of teeth with the second portion of the first segment of suture cooperates to resist further displacement of the first segment of suture in the first direction, and wherein the first plurality of teeth and the second plurality of teeth are each configured to allow the first segment of suture to be displaced in a second direction that is opposite to the first direction, and wherein the first cam grip is configured to rotate in a first rotational direction about the first rotational axis when the first plurality of teeth engages the first portion of the first segment of suture when the first segment of suture is displaced in the first direction and wherein the second cam grip is configured to rotate in a second rotational direction about the second rotational axis when the second plurality of teeth engages the second portion of the first segment of suture when the first segment of suture is displaced in the first direction, and wherein the first cam base is substantially planar and the first rotational axis that extends through the first cam base is normal to the plane defined by the first cam base, and wherein the second cam base is substantially planar and the second rotational axis that extends through the second cam base is normal to the plane defined by the second cam base.

2. The apparatus for suture management of claim 1, wherein the perimeter edge of the first cam base has a circular shape and the perimeter edge of the second cam base has a circular shape.

3. The apparatus for suture management of claim 1, wherein the first rotational direction is opposite to the second rotational direction.

4. The apparatus for suture management of claim 1, further comprising:
   a third cam grip comprising:
      a third cam base at least partially defined by a perimeter edge; and
      a third cam gripping arm coupled to the third cam base, the third cam gripping arm having an edge portion comprising a third plurality of teeth,
      wherein the third cam grip is configured to rotate about a third rotational axis that extends through the third cam base; and
   a fourth cam grip comprising:
      a fourth cam base at least partially defined by a perimeter edge; and
      a fourth cam gripping arm coupled to the fourth cam base, the fourth cam gripping arm having an edge portion comprising a fourth plurality of teeth,
      wherein the fourth cam grip is configured to rotate within the third cam pocket about a fourth rotational axis that extends through the fourth cam base,
   wherein the third cam grip is oriented such that the third plurality of teeth is adapted to engage a first portion of a second segment of suture when the second segment of suture is displaced in a third direction and the fourth cam grip is oriented such that the fourth plurality of teeth is adapted to engage a second portion of the second segment of suture when the second segment of suture is displaced in the third direction, wherein the engagement of the third plurality of teeth with the first portion of the second segment of suture and the engagement of the fourth plurality of teeth with the second portion of the second segment of suture cooperates to resist further displacement of the second segment of suture in the third direction, and wherein the third plurality of teeth and the fourth plurality of teeth are each configured to allow the second segment of suture to be displaced in a fourth direction that is opposite to the third direction, and wherein the third cam grip is configured to rotate in a third rotational direction about the third rotational axis when the third plurality of teeth engages the first portion of the second segment of suture when the second segment of suture is displaced in the third direction and wherein the fourth cam grip is configured to rotate in a fourth rotational direction about the fourth rotational axis when the fourth plurality of teeth engages the second portion of the second segment of suture when the second segment of suture is displaced in the third direction.

5. The apparatus for suture management of claim 4, wherein the third rotational axis is coaxially aligned with the second rotational axis.

6. The apparatus for suture management of claim 4, wherein the third direction is the same as the first direction and the fourth direction is the same as the second direction.

7. The apparatus for suture management of claim 4, wherein the third rotational direction is the same as the first rotational direction and the fourth rotational direction is the same as the second rotational direction.

8. The apparatus for suture management of claim 4, wherein the second cam base has a top surface that is substantially planar and the third cam base has a bottom surface that is substantially planar, and the top surface of the second cam base is in contact with or immediately adjacent to the bottom surface of the third cam base.

9. The apparatus for suture management of claim 8, wherein the third cam gripping arm has a bottom surface that is substantially planar, and the bottom surface of the third cam base is substantially coplanar with the bottom surface of the third cam gripping arm, and
   wherein the second cam gripping arm has a top surface and the top surface of the second cam gripping arm is not coplanar with the top surface of the second cam base.

10. The apparatus for suture management of claim 9, wherein the top surface of the second cam gripping arm is substantially planar.

11. The apparatus for suture management of claim 1, wherein the first rotational axis is parallel to the second rotational axis.

12. The apparatus for suture management of claim 1, wherein the first cam gripping arm has a top surface that is substantially planar and the first cam base has a top surface that is substantially planar, and the top surface of the first cam gripping arm is substantially coplanar with the top surface of the first cam base, and
   wherein the second cam gripping arm has a top surface and the second cam base has a top surface that is substantially planar, and the top surface of the second cam gripping arm is not coplanar with the top surface of the second cam base.

13. The apparatus for suture management of claim 12, wherein the top surface of the second cam gripping arm is substantially planar.

14. The apparatus for suture management of claim 1, further comprising:
   a housing portion comprising:
      a first cam pocket defined in a first portion of the housing portion, wherein the first cam base is disposed within the first cam pocket such that the perimeter edge of the first cam base is adjacent to or in contact with one or more surfaces defining the first cam pocket to at least partially retain the first cam base within the first cam pocket; and a second cam pocket defined in a second portion of the housing portion, wherein the second cam base is disposed within the second cam pocket such that the perimeter edge of the second cam base is adjacent to or in contact with one or more surfaces defining the second cam pocket to at least partially retain the second cam base within the second cam pocket.

15. The apparatus for suture management of claim 14, the housing portion further comprising:

a first suture slot at least partially defined by one or more exterior surfaces of the housing, wherein the first suture slot is configured to receive the first segment of suture, and wherein a portion of the first plurality of teeth of the first cam grip extends into a first portion of the first suture slot to engage the first portion of the first segment of suture when the first segment of suture is displaced in the first direction, and wherein a portion of the second plurality of teeth of the second cam grip extends into a second portion of the first suture slot to engage the second portion of the first segment of suture when the first segment of suture is displaced in the first direction.

16. An apparatus for suture management, the apparatus comprising:

a first cam grip comprising:
a first cam base at least partially defined by a perimeter edge; and
a first cam gripping arm coupled to the first cam base, the first cam gripping arm having an edge portion comprising a first plurality of teeth,
wherein the first cam grip is configured to rotate about a first rotational axis that extends through the first cam base, a second cam grip comprising:
a second cam base at least partially defined by a perimeter edge; and
a second cam gripping arm coupled to the second cam base, the second cam gripping arm comprising an edge portion having a second plurality of teeth,
wherein the second cam grip is configured to rotate about a second rotational axis that extends through the second cam base, wherein the first cam grip is oriented such that the first plurality of teeth is adapted to engage a first portion of a first segment of suture when the first segment of suture is displaced in a first direction and the second cam grip is oriented such that the second plurality of teeth is adapted to engage a second portion of the first segment of suture when the first segment of suture is displaced in the first direction, wherein the engagement of the first plurality of teeth with the first portion of the first segment of suture and the engagement of the second plurality of teeth with the second portion of the first segment of suture cooperates to resist further displacement of the first segment of suture in the first direction, and wherein the first plurality of teeth and the second plurality of teeth are each configured to allow the first segment of suture to be displaced in a second direction that is opposite to the first direction, and wherein the first cam grip is configured to rotate in a first rotational direction about the first rotational axis when the first plurality of teeth engages the first portion of the first segment of suture when the first segment of suture is displaced in the first direction and wherein the second cam grip is configured to rotate in a second rotational direction about the second rotational axis when the second plurality of teeth engages the second portion of the first segment of suture when the first segment of suture is displaced in the first direction, and wherein the first cam gripping arm has a top surface that is substantially planar and the first cam base has a top surface that is substantially planar, and the top surface of the first cam gripping arm is substantially coplanar with the top surface of the first cam base, and wherein the second cam gripping arm has a top surface and the second cam base has a top surface that is substantially planar, and the top surface of the second cam gripping arm is not coplanar with the top surface of the second cam base.

17. The apparatus for suture management of claim 16, wherein the top surface of the second cam gripping arm is substantially planar.

18. An apparatus for suture management, the apparatus comprising:

a first cam grip comprising:
a first cam base at least partially defined by a perimeter edge; and
a first cam gripping arm coupled to the first cam base, the first cam gripping arm having an edge portion comprising a first plurality of teeth,
wherein the first cam grip is configured to rotate about a first rotational axis that extends through the first cam base, a second cam grip comprising:
a second cam base at least partially defined by a perimeter edge; and
a second cam gripping arm coupled to the second cam base, the second cam gripping arm comprising an edge portion having a second plurality of teeth,
wherein the second cam grip is configured to rotate about a second rotational axis that extends through the second cam base, wherein the first cam grip is oriented such that the first plurality of teeth is adapted to engage a first portion of a first segment of suture when the first segment of suture is displaced in a first direction and the second cam grip is oriented such that the second plurality of teeth is adapted to engage a second portion of the first segment of suture when the first segment of suture is displaced in the first direction, wherein the engagement of the first plurality of teeth with the first portion of the first segment of suture and the engagement of the second plurality of teeth with the second portion of the first segment of suture cooperates to resist further displacement of the first segment of suture in the first direction, and wherein the first plurality of teeth and the second plurality of teeth are each configured to allow the first segment of suture to be displaced in a second direction that is opposite to the first direction, and wherein the first cam grip is configured to rotate in a first rotational direction about the first rotational axis when the first plurality of teeth engages the first portion of the first segment of suture when the first segment of suture is displaced in the first direction and wherein the second cam grip is configured to rotate in a second rotational direction about the second rotational axis when the second plurality of teeth engages the second portion of the first segment of suture when the first segment of suture is displaced in the first direction;
a third cam grip comprising:
   a third cam base at least partially defined by a perimeter edge; and
   a third cam gripping arm coupled to the third cam base, the third cam gripping arm having an edge portion comprising a third plurality of teeth,
   wherein the third cam grip is configured to rotate about a third rotational axis that extends through the third cam base; and
a fourth cam grip comprising:
   a fourth cam base at least partially defined by a perimeter edge; and
   a fourth cam gripping arm coupled to the fourth cam base, the fourth cam gripping arm having an edge portion comprising a fourth plurality of teeth,
   wherein the fourth cam grip is configured to rotate within the third cam pocket about a fourth rotational axis that extends through the fourth cam base,
wherein the third cam grip is oriented such that the third plurality of teeth is adapted to engage a first portion of a second segment of suture when the second segment of suture is displaced in a third direction and the fourth cam grip is oriented such that the fourth plurality of teeth is adapted to engage a second portion of the second segment of suture when the second segment of suture is displaced in the third direction, wherein the engagement of the third plurality of teeth with the first portion of the second segment of suture and the engagement of the fourth plurality of teeth with the second portion of the second segment of suture cooperates to resist further displacement of the second segment of suture in the third direction, and
wherein the third plurality of teeth and the fourth plurality of teeth are each configured to allow the second segment of suture to be displaced in a fourth direction that is opposite to the third direction, and wherein the third cam grip is configured to rotate in a third rotational direction about the third rotational axis when the third plurality of teeth engages the first portion of the second segment of suture when the second segment of suture is displaced in the third direction and wherein the fourth cam grip is configured to rotate in a fourth rotational direction about the fourth rotational axis when the fourth plurality of teeth engages the second portion of the second segment of suture when the second segment of suture is displaced in the third direction.

19. The apparatus for suture management of claim 18, wherein the third rotational axis is coaxially aligned with the second rotational axis.

20. The apparatus for suture management of claim 18, wherein the third direction is the same as the first direction and the fourth direction is the same as the second direction.

21. The apparatus for suture management of claim 18, wherein the third rotational direction is the same as the first rotational direction and the fourth rotational direction is the same as the second rotational direction.

22. The apparatus for suture management of claim 18, wherein the second cam base has a top surface that is substantially planar and the third cam base has a bottom surface that is substantially planar, and the top surface of the second cam base is in contact with or immediately adjacent to the bottom surface of the third cam base.

23. The apparatus for suture management of claim 22, wherein the third cam gripping arm has a bottom surface that is substantially planar, and the bottom surface of the third cam base is substantially coplanar with the bottom surface of the third cam gripping arm, and
   wherein the second cam gripping arm has a top surface and the top surface of the second cam gripping arm is not coplanar with the top surface of the second cam base.

24. The apparatus for suture management of claim 23, wherein the top surface of the second cam gripping arm is substantially planar.

* * * * *